(12) United States Patent
Armstrong et al.

(10) Patent No.: US 6,981,982 B2
(45) Date of Patent: Jan. 3, 2006

(54) METHOD OF PRODUCING LOW PROFILE STENT AND GRAFT COMBINATION

(75) Inventors: Joseph R. Armstrong, Flagstaff, AZ (US); Edward H. Cully, Flagstaff, AZ (US); Mark J. Ulm, Flagstaff, AZ (US); Michael J. Vonesh, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 382 days.

(21) Appl. No.: 10/083,451

(22) Filed: Feb. 25, 2002

(65) Prior Publication Data

US 2002/0138129 A1 Sep. 26, 2002

Related U.S. Application Data

(62) Division of application No. 09/235,458, filed on Jan. 22, 1999, now abandoned.

(51) Int. Cl.
*A61M 29/00* (2006.01)
(52) U.S. Cl. .......................... 606/198; 29/282
(58) Field of Classification Search .............. 606/1, 606/108, 198; 623/1.11–1.44; 29/282, 516
See application file for complete search history.

(56) References Cited

U.S. PATENT DOCUMENTS

| | | | |
|---|---|---|---|
| 3,953,566 A | 4/1976 | Gore | 264/288 |
| 3,962,153 A | 6/1976 | Gore | 260/2.5 R |
| 4,096,227 A | 6/1978 | Gore | 264/210 R |
| 4,187,390 A | 2/1980 | Gore | 174/102 R |
| 4,512,338 A | 4/1985 | Balko et al. | 128/1 R |
| 4,562,596 A | 1/1986 | Kornberg | 623/1 |
| 4,902,423 A | 2/1990 | Bacino | 210/500.36 |
| 5,042,707 A | 8/1991 | Taheri | 606/213 |
| 5,183,085 A | 2/1993 | Timmermans | 140/89 |
| 5,275,622 A | 1/1994 | Lazarus et al. | 623/1 |
| 5,316,023 A | 5/1994 | Palmaz et al. | 128/898 |
| 5,370,683 A | 12/1994 | Fontaine | 623/1 |
| 5,405,378 A | 4/1995 | Strecker | 623/1 |
| 5,474,563 A | 12/1995 | Myler et al. | 606/108 |
| 5,476,589 A | 12/1995 | Bacino | 210/500.36 |
| 5,489,295 A | 2/1996 | Piplani et al. | 623/1 |
| 5,522,961 A | 6/1996 | Leonhardt | 156/252 |
| 5,546,646 A | 8/1996 | Williams et al. | 29/407.08 |
| 5,562,724 A | 10/1996 | Vorwerk et al. | 623/1 |
| 5,575,818 A | 11/1996 | Pinchuk | 623/1 |
| 5,591,195 A | 1/1997 | Taheri et al. | 606/194 |

(Continued)

FOREIGN PATENT DOCUMENTS

EP 0 792 627 A2 9/1997

(Continued)

*Primary Examiner*—Vy Bui
(74) *Attorney, Agent, or Firm*—David J. Johns

(57) ABSTRACT

Large diameter self-expanding endoprosthetic devices, such as stents and stent grafts for delivery to large diameter vessels, such as the aorta, are disclosed having very small compacted delivery dimensions. Devices with deployed dimensions of 26 to 40 mm or more are disclosed that are compacted to extremely small dimensions of 5 mm or less, enabling percutaneous delivery of said devices without the need for surgical intervention. Compaction efficiencies are achieved by combining unique material combinations with new forms of restraining devices, compaction techniques, and delivery techniques. These inventive devices permit consistent percutaneous delivery of large vessel treatment devices. Additionally, small endoprosthetic devices are disclosed that can be compacted to extremely small dimensions for delivery through catheter tubes of less than 1 mm diameter.

11 Claims, 15 Drawing Sheets

U.S. PATENT DOCUMENTS

| | | | |
|---|---|---|---|
| 5,617,878 A | 4/1997 | Taheri | 128/898 |
| 5,626,604 A | 5/1997 | Cottone, Jr. | 606/198 |
| 5,628,783 A | 5/1997 | Quiachon et al. | 623/1 |
| 5,630,830 A | 5/1997 | Verbeek | 606/198 |
| 5,632,772 A | 5/1997 | Alcime et al. | 623/1 |
| 5,639,278 A | 6/1997 | Dereume et al. | 623/1 |
| 5,662,702 A | 9/1997 | Keranen | 623/1 |
| 5,672,169 A | 9/1997 | Verbeek | 606/1 |
| 5,676,671 A | 10/1997 | Inoue | 606/108 |
| 5,676,697 A | 10/1997 | McDonald | 623/1 |
| 5,683,451 A | 11/1997 | Lenker et al. | 623/1 |
| 5,693,029 A | 12/1997 | Leonhardt | 604/264 |
| 5,695,517 A | 12/1997 | Marin et al. | 606/198 |
| 5,700,285 A | 12/1997 | Myers et al. | 623/1 |
| 5,713,917 A | 2/1998 | Leonhardt et al. | 606/194 |
| 5,716,396 A | 2/1998 | Williams, Jr. | 623/1 |
| 5,718,973 A | 2/1998 | Lewis et al. | 428/36.5 |
| 5,725,519 A | 3/1998 | Penner et al. | 606/1 |
| 5,735,892 A | 4/1998 | Myers et al. | 623/1 |
| 5,738,674 A | 4/1998 | Williams et al. | 606/1 |
| 5,746,764 A | 5/1998 | Green et al. | 606/194 |
| 5,776,181 A | 7/1998 | Lee et al. | 623/1 |
| 5,800,515 A | 9/1998 | Nadal et al. | 623/1 |
| 5,800,519 A | 9/1998 | Sandock | 623/1 |
| 5,800,520 A | 9/1998 | Fogarty et al. | 623/1 |
| 5,810,838 A | 9/1998 | Solar | 606/108 |
| 5,810,870 A | 9/1998 | Myers et al. | 606/198 |
| 5,810,873 A | 9/1998 | Morales | 606/198 |
| 5,817,126 A | 10/1998 | Imran | 606/198 |
| 5,824,037 A | 10/1998 | Fogarty et al. | 623/1 |
| 5,824,040 A | 10/1998 | Cox et al. | 623/1 |
| 5,824,054 A | 10/1998 | Khosravi et al. | 623/1 |
| 5,824,055 A | 10/1998 | Spiridigliozzi et al. | 623/1 |
| 5,833,707 A | 11/1998 | McIntyre et al. | 606/198 |
| 5,836,952 A | 11/1998 | Davis et al. | 606/108 |
| 5,836,965 A | 11/1998 | Jendersee et al. | 606/198 |
| 5,855,598 A | 1/1999 | Pinchuk | 623/1 |
| 5,860,966 A | 1/1999 | Tower | 606/1 |
| 5,871,536 A | 2/1999 | Lazarus | 623/1 |
| 5,893,852 A | 4/1999 | Morales | 606/108 |
| 5,893,867 A * | 4/1999 | Bagaoisan et al. | 606/198 |
| 5,911,452 A | 6/1999 | Yan | 29/516 |
| 5,920,975 A | 7/1999 | Morales | 29/282 |
| 5,925,075 A | 7/1999 | Myers et al. | 623/1 |
| 5,931,851 A | 8/1999 | Morales | 606/194 |
| 5,944,735 A | 8/1999 | Green et al. | 606/194 |
| 5,947,993 A | 9/1999 | Morales | 606/198 |
| 5,971,992 A | 10/1999 | Solar | 606/108 |
| 5,972,016 A | 10/1999 | Morales | 606/198 |
| 5,972,028 A | 10/1999 | Rabenau et al. | 623/1 |
| 5,972,441 A | 10/1999 | Campbell et al. | 428/34.1 |
| 5,974,652 A | 11/1999 | Kimes et al. | 29/516 |
| 5,976,181 A | 11/1999 | Whelan et al. | 623/1 |
| 5,976,650 A | 11/1999 | Campbell et al. | 428/35.7 |
| 5,992,000 A | 11/1999 | Humphrey et al. | 29/516 |
| 5,993,481 A | 11/1999 | Marcade et al. | 623/1 |
| 5,993,489 A | 11/1999 | Lewis et al. | 628/1 |
| 6,009,614 A | 1/2000 | Morales | 29/516 |
| 6,015,431 A | 1/2000 | Thornton et al. | 623/1 |
| 6,018,857 A | 2/2000 | Duffy et al. | 29/407.01 |
| 6,024,737 A | 2/2000 | Morales | 606/1 |
| 6,025,044 A | 2/2000 | Campbell et al. | 428/36.91 |
| 6,027,779 A | 2/2000 | Campbell et al. | 428/36.91 |
| 6,027,811 A | 2/2000 | Campbell et al. | 428/411.1 |
| 6,051,001 A | 4/2000 | Borghi | 606/108 |
| 6,051,002 A | 4/2000 | Morales | 606/108 |
| 6,051,020 A | 4/2000 | Goicoechea et al. | 623/1 |
| 6,063,092 A | 5/2000 | Shin | 606/108 |
| 6,063,102 A | 5/2000 | Morales | 606/198 |
| 6,066,156 A | 5/2000 | Yan | 606/192 |
| 6,074,381 A | 6/2000 | Dinh et al. | 606/1 |
| 6,077,296 A | 6/2000 | Shokoohi et al. | 623/1 |
| 6,082,990 A | 7/2000 | Jackson et al. | 425/517 |
| 6,092,273 A | 7/2000 | Villareal | 29/516 |
| 6,096,027 A | 8/2000 | Layne | 606/1 |
| 6,108,886 A | 8/2000 | Kimes et al. | 29/280 |
| 6,167,605 B1 * | 1/2001 | Morales | 29/282 |

FOREIGN PATENT DOCUMENTS

| | | |
|---|---|---|
| EP | 0 819 412 A2 | 1/1998 |
| WO | 97/21403 | 6/1997 |
| WO | 98/36708 | 2/1998 |
| WO | 98/19632 | 5/1998 |
| WO | 98/27894 | 7/1998 |
| WO | 98/38946 | 9/1998 |
| WO | 99/39662 | 2/1999 |

* cited by examiner

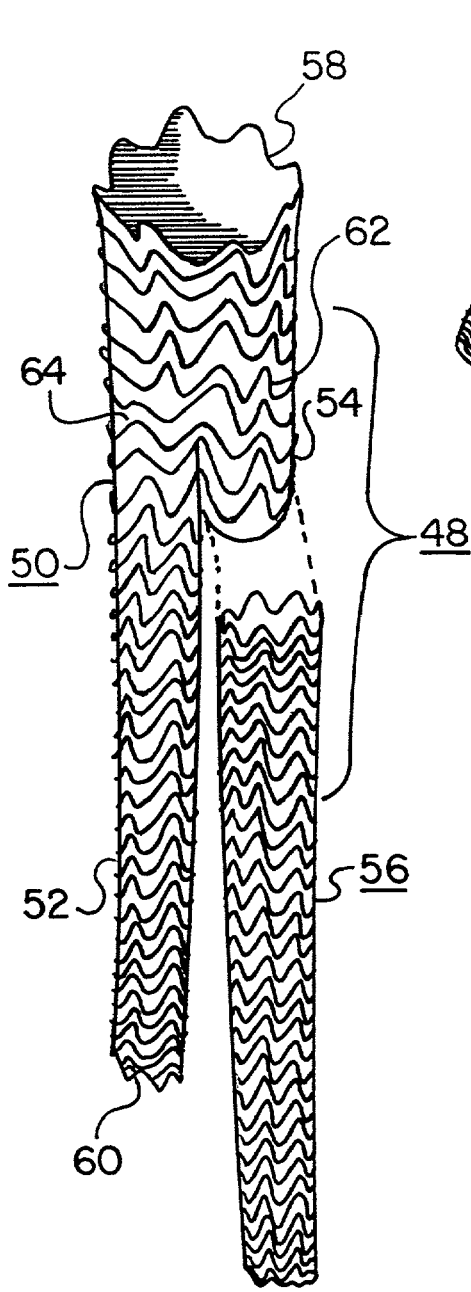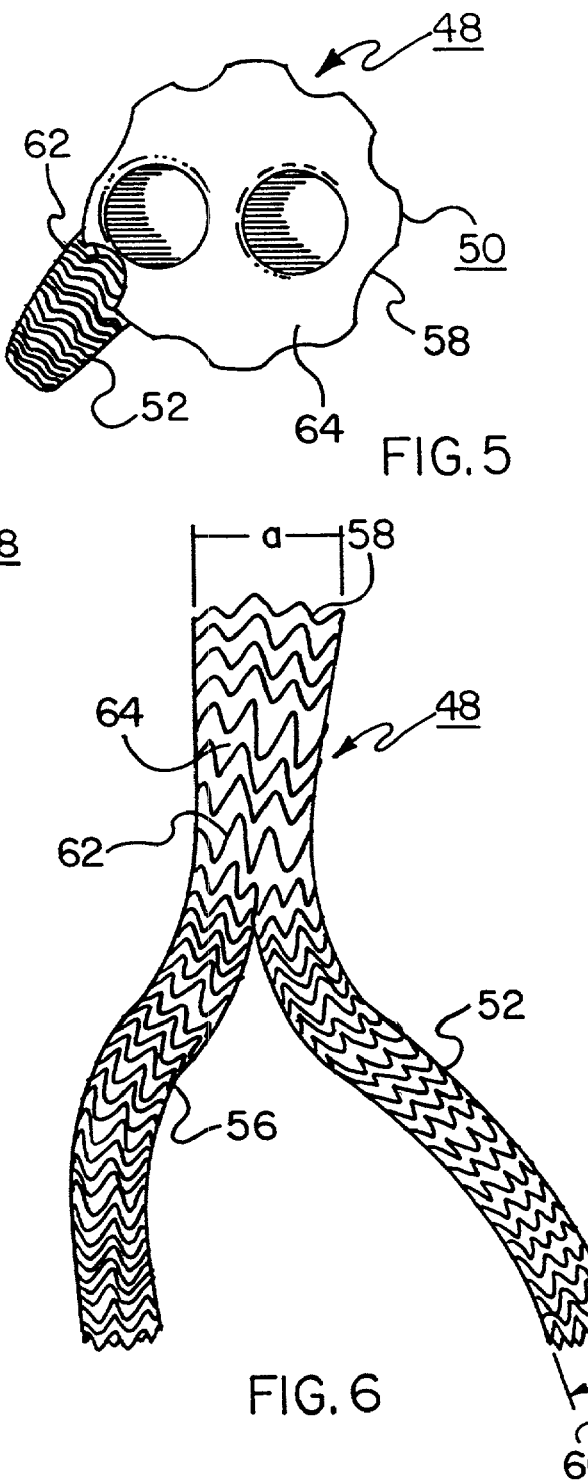
FIG. 4  FIG. 5  FIG. 6

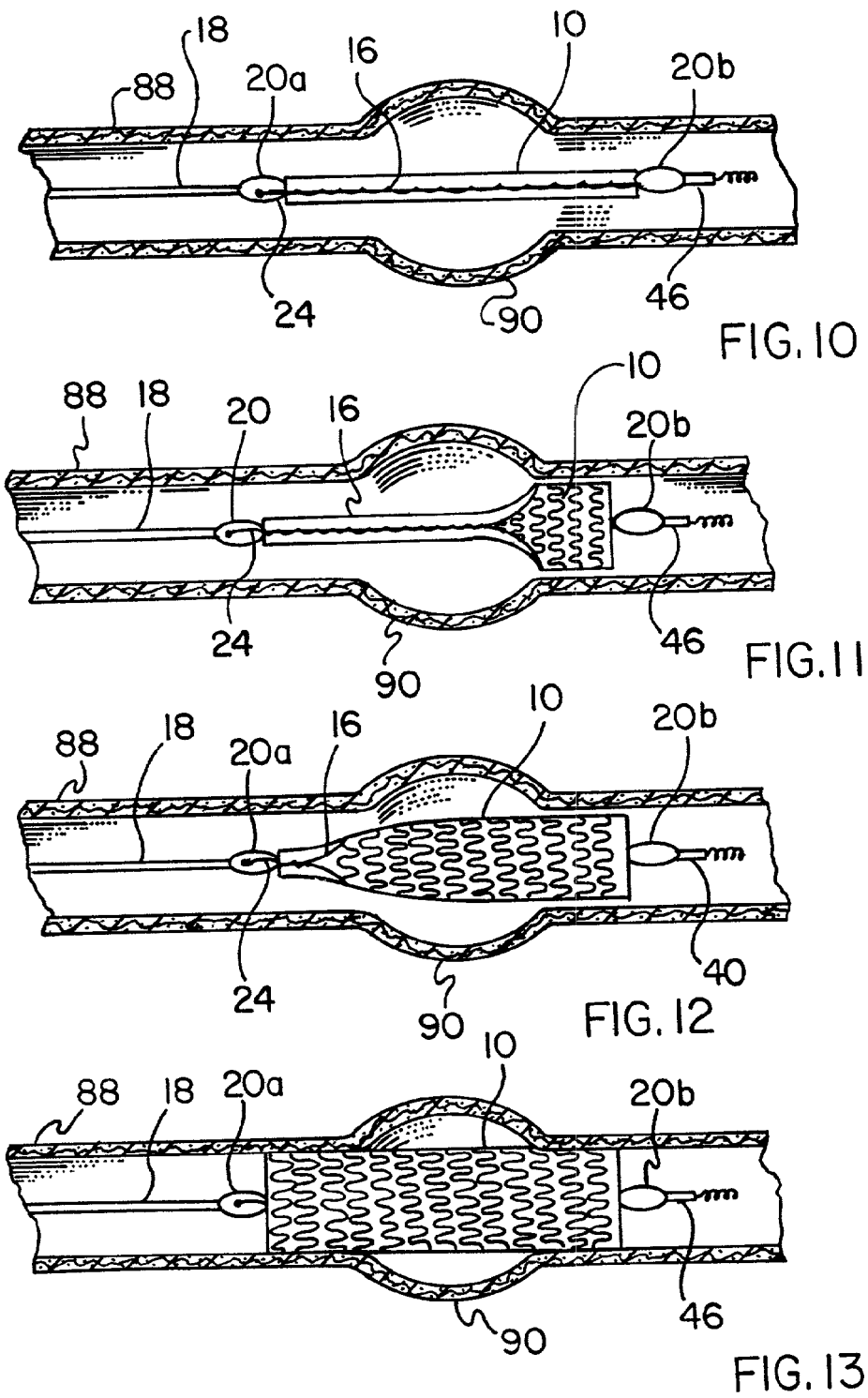

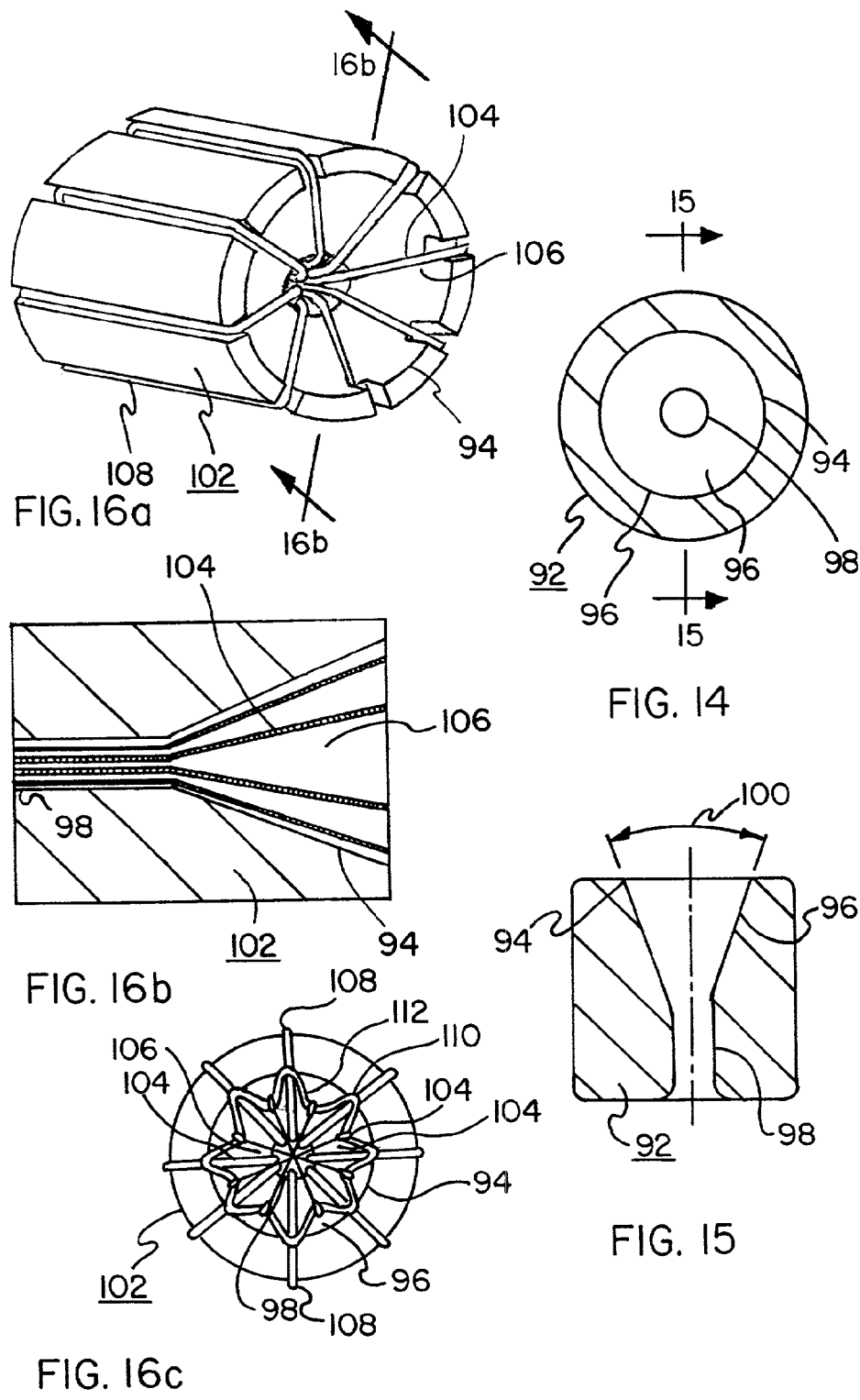

METHOD OF PRODUCING LOW PROFILE STENT AND GRAFT COMBINATION

CROSS REFERENCE TO RELATED APPLICATIONS

The present application is a division of now abandoned U.S. patent application Ser. No. 09/235,458, filed Jan. 22, 1999.

BACKGROUND OF THE INVENTION

1. Field of the Invention

The present invention relates to methods of producing endoprosthetic devices, such as stents and stent-grafts, that are used to repair and/or treat diseased or damaged vessels and other structures within a body, and particularly to such devices that can be introduced at small delivery profiles and then enlarged in place.

2. Description of Related Art

Stents and stent-grafts are used in the treatment of vascular and other disease. They are particularly useful for treatment of vascular or arterial occlusion or stenosis typically associated with vessels narrowed by disease. Intraluminal stents and stent-grafts function to hold these vessels open mechanically. In some instances, they may be used subsequent to, or as an adjunct to, a balloon angioplasty procedure. Stent-grafts, which include a graft cover, are also particularly useful for the treatment of aneurysms. An aneurysm may be characterized as a sac formed by the dilatation of a wall or an artery, vein, or vessel. Typically the aneurysm is filled with fluid or clotted blood. The stent-graft provides a graft liner to reestablish a flow lumen through the aneurysm as well as a stent structure to support the graft and to resist occlusion or stenosis.

Treatment of a bifurcation site afflicted with such defects as an occlusion, stenosis, or aneurysm is a particularly demanding application for either stents or stent-grafts. A bifurcation site is generally where a single lumen or artery (often called the "trunk") splits into two lumens or arteries (often called "branches"), such as in a "Y" configuration. For example, one such bifurcation site is found within the human body at the location where the abdominal aorta branches into the left and right (or ipsilateral and contralateral, respectively) iliac arteries.

When a defect, such as an aneurysm, is located very close to the bifurcation of a trunk into two branches, treatment becomes especially difficult. One reason for this difficulty is that neither the trunk nor either of the branches provides a sufficient portion of healthy vessel wall proximal and distal to the defect to which a straight section of single lumen stent or stent-graft can be secured. The stent or stent-graft must span the bifurcation site and yet allow relatively undisturbed flow through each of the branches and trunk.

Stents and stent-grafts offer considerable advantages over conventional surgery. Because they are comparatively less invasive, reduced mortality and morbidity, combined with shorter hospital stay, are the more significant advantages of stent and stent-graft therapies. Low profile endoprostheses (that is, endoprostheses that can be compacted into a small size for delivery) continue to be developed that enable the introduction of such devices through progressively smaller holes cut or punched through vessel walls. These low profile devices reduce blood loss and procedural morbidity compared to higher profile devices. Preferably, low profile devices should also be more flexible in the compacted delivery state. Devices that are more flexible during delivery better enable passage through tortuous vessels en route to the desired delivery site. Furthermore, thinner walled devices may cause less flow disturbance at the inlet and outlet to the graft.

The preferred device is one that can be introduced "percutaneously," that is through a small transcutaneous incision or puncture 12 French (F) (4.0 mm) or less in diameter. Percutaneous delivery of a stent or stent-graft can often be done on an out-patient basis, and is typically associated with decreased patient morbidity, decreased time to patient ambulation, decreased procedural time, and potential reduction in health care delivery cost compared to surgical delivery of endoprostheses.

A "stent-graft" is formed by providing a covering on either the inside, outside, or both surfaces of the stent. These covered devices can provide a number of improvements over conventional uncovered stents. First, the cover may provide a fluid barrier (that is, either liquid or gas or both), prohibiting transmural fluid leakage from the inside to the outside of the device, or inhibiting transmural infiltration of fluids into the lumen of the device, or both. Second, covered devices can also limit tissue encroachment into the device over time. Third, it is believed that a covered device may provide an improved flow surface, which may aid in longer and more effective operating life for the device.

While covered stent devices have many benefits, unfortunately current covered-stents used for the treatment of disease of large vessels (e.g., thoracic or abdominal aortic vessels) generally require a surgical incision to provide a large enough access site to deliver such devices. Virtually all such devices currently are too large for less-invasive percutaneous delivery.

The current standard procedure for stent and stent-graft delivery is outlined below. The stent or stent-graft device is reduced in diameter ("compacted") to enable it to be introduced through small incisions or punctures via a transcatheter approach. "Self-expanding" devices inherently increase in diameter once a restraining mechanism is removed. "Restraining mechanisms" typically fit over part or all of the outer surface of compacted self-expanding devices to constrain them in a reduced diameter on the delivery catheter until deployment. "Deployment" is the term given to increasing the diameter of these intraluminal devices and subsequent detachment of the device from the delivery catheter. "Deployed inner diameter" as used herein is the device inner diameter measured immediately subsequent to releasing the device from its restraining mechanism in a 36–40° C. water bath and pressurizing the device to 1 Atm with an appropriately sized balloon dilatation catheter. An appropriately sized balloon will transmit the 1 Atm pressure to the device. For devices that cannot withstand a 1 Atm pressure, the deployed inner diameter corresponds to the size of the device immediately prior to rupture. For devices that require balloon expansion, the applied pressure is that pressure required to fully deploy the device to its intended dimensions.

Once self-expanding devices are properly positioned within the body, the restraining mechanism is removed, thereby deploying and anchoring the device. "Balloon-expandable" devices require the use of a balloon catheter or other means of dilatation within the recipient luminal structure for deployment and anchoring. Such devices are typically mounted and delivered on top of a balloon, which inherently increases their delivery profile.

As has been noted, percutaneous delivery is almost always preferred but is difficult or impossible to achieve for larger devices. A device (including restraining mechanism, if any) with a maximum outer dimension of no more than 10 French (F) (3.3 mm) can almost always be delivered percutaneously. More skilled physicians may opt to place devices percutaneously with dimensions of 12 F (4.0 mm), 13 F (4.3 mm), 14 F (4.7 mm), or more, although bleeding and other complications increase markedly with increasing access site size. Generally herein, a "percutaneous" device is considered to be a device that has an outer diameter in a delivered state of no more than 12 F.

Devices are generally placed into the body through percutaneously or surgically placed introducer sheaths that are sized according to their inner diameter. The wall thicknesses of these sheaths typically adds about 2 F to the size of the device. That is, a 12 F introducer sheath has about a 14 F outer diameter. "French" measurements used herein define the size of a hole through which a device will pass. For example, device with a measurement of "10 French" will pass through a 10 French hole (which has a diameter of 3.3 mm). A device need not have a circular cross-section in order to pass through a circular 10 French hole so long as the hole is large enough to accommodate the widest cross-section dimension of the device. The delivery size of an intraluminal stent-graft device is a function of stent geometry, stent-graft compacting efficiency, volume of the stent, volume of the stent cover, thickness of the restraining mechanism (if any), and the outer diameter of any guidewire or catheter within the lumen of the compacted device.

There are many problems encountered in attempting to compact a device into its smallest deliverable dimensions. First, the material of the stent element itself takes up a certain volume. If a graft component is added, this further increases the bulk of the device. Accordingly, there are absolute limits to compaction based strictly on the volume of the component parts.

Second, all known stent element designs provide the stent with crush-resistance (which is required if the stent is to have any structural value in holding open a vessel). This resistance to crushing further confounds attempts to tightly compact the device—with the risk that over-compacting the stent may damage its crush-resistance (and thus its structural value as a stent). On the other hand, less resilient stent devices might be more receptive to compaction, but are less effective in holding open the vessel once deployed.

Third, the graft material is also at risk of damage during compacting. Since the stent and the graft are compacted together, the stent element must be designed and compacted in such a way that it will not damage the graft when the two are compressed together.

Fourth, any compaction of a stent or stent-graft will likely tend to reduce the flexibility of the compacted device. Extreme compaction may produce a compacted device that is so inflexible that it will not negotiate tortuous paths in the body.

Fifth, as has been noted, currently available delivery devices and techniques (e.g., introducer sheaths, guidewires, delivery catheters, etc.) also add bulk to the device—generally adding about 2 to 3 F (0.67 to 1 mm) or more to the profile of the apparatus that must be delivered through the vascular access site.

Sixth, there are covered stents available today that can be compressed into small delivery profiles, but these devices undergo extreme elongation in their compressed state, with extreme foreshortening when transitioned to their deployed dimensions. These extremes in device length between compact and deployed dimensions make these devices difficult to properly position and deploy. Additionally, these devices tend to have less resilient stent structures. Finally, perhaps the greatest deficiency of these devices is that they must be covered with a material that can likewise undergo extreme elongation and contraction to match the longitudinal behavior of the stent element. As a result, preferred biocompatible graft materials such as polytetrafluoroethylene (PTFE) and woven DACRON® polyester are not readily used on these devices since neither is capable of extreme stretching and rebounding.

Results have been reported that a braided stent graft with a highly porous elastomeric covering allows the stent, when compacted for delivery, to be substantially elongated. Distributing the stent cross-sectional mass over a longer length (up to 40% length change) allows percutaneous delivery of a large device. Although these devices can fit through smaller delivery sites of 8 to 10 F, exact placement is often difficult because of the significant longitudinal retraction or recoil of the stent graft as it reaches its deployed size. The design of this stent relies on extreme elongation to achieve its compaction, hence undesirable foreshortening of the device naturally occurs during deployment. As a result, this design cannot accommodate a longitudinal strength member that would resist elongation during compaction of the device. In order to allow the stent frame to undergo extreme changes in length, elastomeric coverings are employed to permit the cover to expand and contract along with the stent frame. The coverings primarily serve as a barrier to the passage of blood and/or tissue or other elements in use, although their stretch and recovery requirements severely limit they types of materials that can be used in this device. Thickness and porosity is also a design limitation for these elastomeric stent coverings. To reduce porosity the coverings often must be thicker (often about 0.05 mm or greater), which can adversely effect delivery profile.

It should be evident from the above description that it is very desirable to provide an endoprosthetic device that can be delivered percutaneously. This is especially true for an endoprosthesis that combines the benefits of both a stent and a graft. However, there currently are a number of serious constraints limiting the ability to compact endoprosthetic devices, and particularly large vessel endoprosthetic devices (for instance, for treatment of aortic diseases and trauma), into their smallest possible delivery profiles.

SUMMARY OF THE INVENTION

The present invention provides methods of substantially reducing the delivery profile of endovascular devices and substantially increasing the ratio of the deployed inner diameter and compacted outer diameter of such devices.

To achieve extremely small delivery profiles, low profile devices of the present invention are constructed using the following techniques: exceptionally thin and strong covers (e.g., expanded polytetrafluoroethylene and/or polyester mesh); small gauge (diameter) wire (e.g., nitinol wire) to construct stent frames or thin-walled cut tubing; stent geometry that enables a high packing efficiency; low mass means of attaching covers to stent frames; and improved methods for compacting stent-grafts. Furthermore, a low profile means of restraining the device in the non-distended (i.e., compacted) state, ready for delivery, are also utilized in the design. Finally, improved delivery techniques that enable the use of lower profile devices are also incorporated.

An important purpose of the present invention is to provide percutaneously deliverable, large diameter stent-graft devices for the treatment of large vessel (e.g., aortic) disease. An endoprosthetic device of the present invention can achieve extremely high compaction efficiencies, containing a stent-graft with a deployed inner diameter of greater than 23 mm into a compacted dimension with a diameter of less than 12 F. This can be achieved with minimal longitudinal length change in the device between its compacted and deployed dimensions.

Further advantages of the present invention are to provide a very low profile covered-stent, and to provide a covered-stent with the broadest deployment range, from the delivery size to the fully extended (i.e., deployed) size. Still another advantage of the present invention is the ability to create very small implantable devices that are capable of being delivered in extremely small compacted dimensions. These and other benefits of the present invention will be appreciated from review of the following description.

DESCRIPTION OF THE DRAWINGS

The operation of the present invention should become apparent from the following description when considered in conjunction with the accompanying drawings, in which:

FIG. 4 is a three-quarter side elevation view of a two-part, modular, large diameter bifurcated stent-graft of the present invention shown in its fully deployed dimension;

FIG. 5 is a top view of the stent-graft of FIG. 4;

FIG. 6 is a side elevation view of the stent-graft of FIG. 4 shown in its deployed orientation (i.e., with the modular components of FIG. 4 joined together);

FIGS. 10 through 13 are side cross-section views of the steps of deploying a straight stent-graft of the present invention within a vessel having an aneurysm, the stent-graft being deployed from a fully compacted dimension in FIG. 10 to a fully deployed dimension in FIG. 13;

FIG. 14 is a top plan view of one embodiment of a tapered die used to compact the stent-graft of the present invention;

FIG. 15 is a side cross-section view of the tapered die of FIG. 14 along section line 15—15;

FIG. 16a is a three-quarter isometric view of another embodiment of a tapered die used to establish a pleated compacted endoprosthesis of the present invention, this tapered die including fluting (i.e., longitudinal ridges) to assist in compaction by forming folded pleats in the device during compaction;

FIG. 16b is a side cross-section view of the tapered die of FIG. 16a along line 16b—16b;

FIG. 16c is a top plan view of the tapered die of FIGS. 16a and 16b showing a circular stent-frame being drawn through the tapered die using tether lines;

DETAILED DESCRIPTION OF THE INVENTION

The present invention is an improved endoprosthetic device, particularly such a device for use in large diameter vessels, that is capable of being compacted into very small delivery dimensions. For instance, stent-graft endoprosthetic devices of the present invention may be formed in large deployed dimensions for thoracic aortic vessels (with diameters of 26, 28, 30 mm or more) or for bifurcated abdominal aortic vessels (with diameters of 23, 25, 27 mm or more) that can be delivered at very small compacted dimensions of 14 F (4.7 mm) or less. In fact, the present invention can even produce large vessel stent-graft devices that can be delivered percutaneously at less than or equal to 12 F (4.0 mm).

Additionally, the compacting technology of the present invention also permits construction of extremely small devices, on the order of 4 mm or less in deployed diameter that can be delivered in a compacted dimension of less than 3 or 2 F (1 or 0.7 mm).

Figure 1:
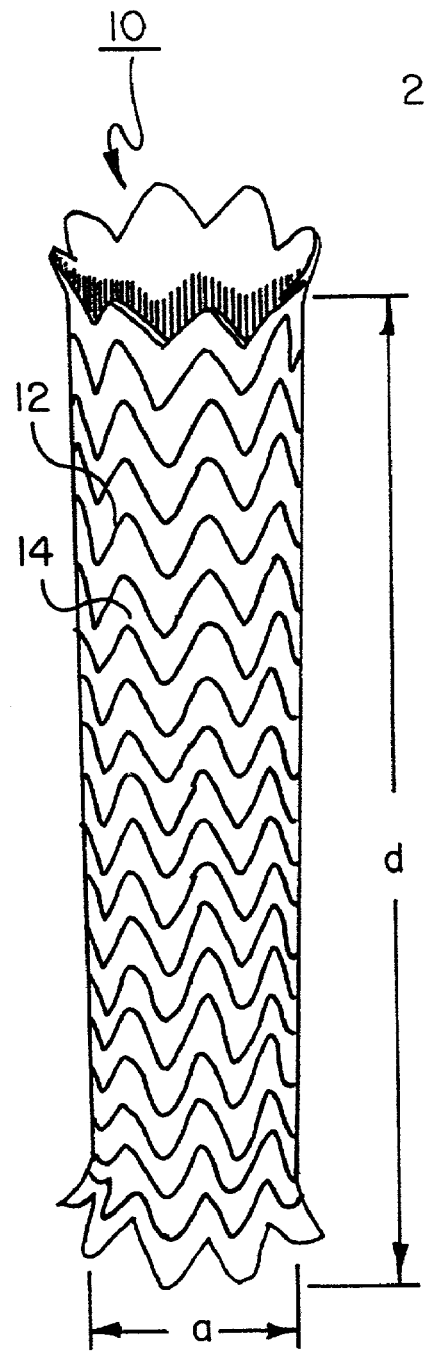
FIG. 1 is three-quarter side elevation view of a large diameter thoracic aortic stent-graft of the present invention shown in its fully deployed dimension.

FIG. 1 illustrates one embodiment of an endoprosthesis 10 of the present invention at its deployed dimension. This endoprosthesis 10 comprises a stent element 12 and a cover 14 attached together to form a stent-graft combination. This particular endoprosthesis 10 is designed for lining a thoracic aortic vessel, for instance to treat an aneurysm therein. Typically this requires the device to have a cross-sectional diameter "a" in its deployed dimension of about 26 mm to 40 mm or more.

Current commercially available stent-graft devices used to treat thoracic aortic aneurysms of this type are delivered in compacted dimensions of about 18 F (6.0 mm) to 27 F (9.0 mm) or more. These compacted dimensions are so large, that percutaneous delivery of these devices is difficult or impossible. Typically delivery of these large vessel endoprostheses requires a surgical cut-down to access deeper but larger blood vessels for device insertion. Alternatively, some large vessel devices available today can be delivered at small delivery profiles, but these devices must undergo extreme and highly undesirable changes in longitudinal length between compacted and deployed dimensions.

Figure 2:
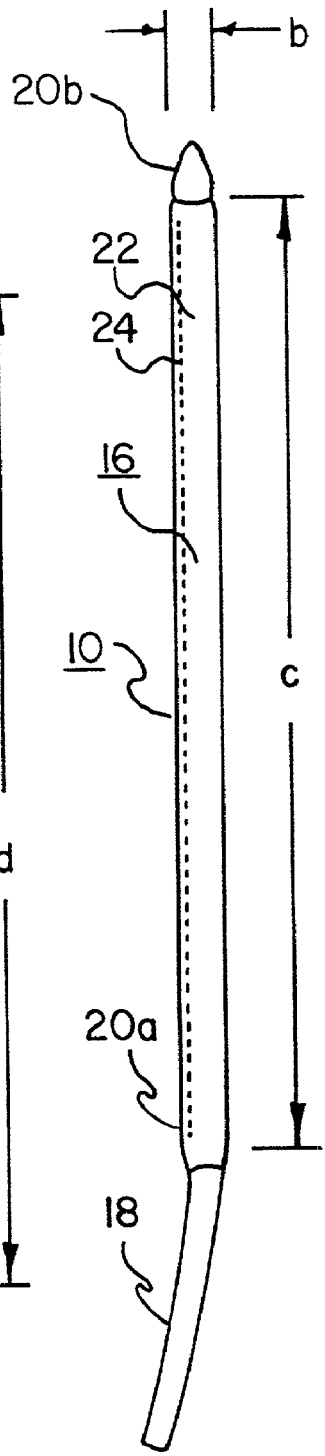
FIG. 2 is a three-quarter side elevation view of a large diameter stent-graft of the present invention shown in its compacted dimension and mounted on a delivery catheter beneath a sleeve-like restraining mechanism.

By contrast, by employing the materials and compaction techniques of the present invention, as described below, the present invention can be reduced to compacted dimensions small enough for percutaneous delivery. Moreover, such extreme compaction can be achieved with minimal elongation or foreshortening of the device between compacted and deployed dimensions. FIG. 2 illustrates a stent-graft endoprosthesis 10 of the present invention presented in compacted dimensions for delivery. With a self-expanding stent-graft 10, the device is contained within a restraining device 16 and mounted on delivery catheter 18. Olives 20a, 20b are provided at the proximal and distal ends of the device as mounted on the delivery catheter to assist in holding the stent-graft in place on the catheter and to aid in guiding the device through smaller vessels.

This embodiment of the present invention employs a restraining device 16 comprising a membrane 22 of material wrapped around the stent-graft 10 and sewn in place with a deployment line 24. Removal of the deployment line 24 will cause the stent-graft device to self-expand to its deployed dimension, such as that illustrated in FIG. 1.

In the compacted dimension shown in FIG. 2, the device as mounted on the catheter has a cross-sectional diameter of "b." With the present invention diameter b comprises 12 F (4.0 mm), 11 F (3.7 mm), 10 F (3.3 mm), 9 F (3.0 mm), 8 F (2.7 mm), (2.3 mm), 6 F (2.0 mm) or less. Preferably the device is compacted to a diameter of 12 F or less, so that conventional delivery apparatus can be employed and percutaneous delivery can still be performed through an introducing sheath of 12 F or less. More preferably, the stent-graft 10 is compacted to under 9 or 8 F, allowing percutaneous delivery through a 9 F delivery apparatus. It should be noted that while the dimension "diameter" is used herein, it should be understood that this dimension is intended to define the effective cross-sectional dimension of the device and is not intended to limit the present invention to devices with circular cross-sectional shapes.

With respect to device length, the thoracic device illustrated in FIGS. 1 and 2 undergoes essentially no change between its compacted longitudinal length "c" and its deployed longitudinal length "d." In this instance, the ratio of c:d is significantly less than 1.25 (i.e., significantly less than a 20% change in length). The endoprostheses of the present invention should undergo less than a 25% change in longitudinal length between its compacted dimension and its deployed dimension. Preferably, the device will undergo less than a 20% change in length, and even more preferably it will undergo less than a 15% or 10% change in length. Most preferably, an endoprosthesis of the present invention will experience less than a 5% change in longitudinal length between its fully compacted dimension and its fully deployed dimension. In this respect, the entire device as deployed is maintained compacted within 25% or less of its deployed longitudinal dimensions, without the need for excessive elongation of the device in its compacted state or the splitting of the device into multiple parts in order to achieve low profile delivery.

In order to achieve the small compacted dimension of the present invention, the first important design element is to employ unique low-profile materials. Cover 14 comprises a thin but strong material that is biocompatible, sufficiently flexible to undergo extreme compaction while returning undamaged to a fully deployed state, and sufficiently strong so as to provide proper support of the vessel walls once deployed. The preferred material comprises polytetrafluoroethylene (PTFE), and especially an expanded PTFE material. This expanded PTFE material is described in U.S. Pat. Nos. 3,953,566, 3,962,153, 4,096,227, 4,187,390, 4,902,423, and 5,476,589, all incorporated by reference. Polyester material, such as woven DACRON® polyester, may also be suitable.

The preferred expanded PTFE material for use in the present invention comprises a material having: a thickness of less than about 0.03 mm, and more preferably less than about 0.004 mm; and a longitudinal matrix tensile strength of more than about 650 MPa, and more preferably more than about 800 MPa. Layers of this material are used to create the stent cover. Note that the thickness of the cover may be less than the sum of the thicknesses of the individual layers because the film tends to decrease in thickness during the heat bonding process used to attach the film to the stent frame. "Thickness" can be measured with a snap gage or an optical comparitor, or by the use of a scanning electron micrograph. "Longitudinal matrix tensile strength" refers to the matrix tensile strength of the material that in the direction that is parallel to the predominant orientation of the fibrils, which corresponds to the higher strength direction of the material. Tensile strength may be determined using an INSTRON tensile tester. For a porous polytetrafluoroethylene (PTFE) material, such as expanded PTFE, matrix tensile strength is determined as the tensile strength of the material multiplied by the quotient of the density of the PTFE polymer and the bulk density of the expanded PTFE material. For the purpose of calculating matrix tensile strength, 2.2 g/cc is used as the value for the PTFE polymer density. Bulk density takes into account any porosity of the expanded PTFE material.

For blood conduit applications, the cover should resist the passage of liquids under pressures of about 150 mm Hg or more. For applications requiring that the cover provide exceptional liquid or gas permeation resistance (for example, a cover that may be required to resist bile permeation), a permeability as quantified by a Gurley Number of greater than about 60 seconds for 1 $cm^2$ of material for 100 cc of air is preferred, and even more preferably a Gurley Number in excess of 100 seconds for 1 $cm^2$ of material for 100 cc of air; a thickness of about 0.05 to 0.25 mm, with a thickness of about 0.10 to 0.20 mm preferred; a water entry pressure of about 34 to 102 kPa or more, with 48 to 62 kPa or more preferred.

The stent element 12 and the cover 14 of the present invention are adhered together (for instance, by an adhesive and/or by a wrap of an adhered film or by bonding the stent element between layers or to layers of the cover) to maintain position of the cover 14 on the endoprosthesis 10. The attachment of the cover 14 to the stent element 12 also restricts the stent element 12 from excessively longitudinally elongating when longitudinal tension is applied to the endoprosthesis 10. It is believed preferable that the cover 14 line the interior of the stent element 12, as shown, but acceptable results may also be achieved with the cover 14 placed on the outside of the stent element 12, with the cover being placed both inside and outside of the stent element 12, or with the stent element 12 being embedded within the cover 14. As such, the term "cover" as used herein is intended to include any generally continuous material that is placed inside of and/or placed outside of and/or mounted integrally with the stent element 12 of the present invention.

In order to achieve the lowest possible profile for the device of the present invention, it is very desirable that the cover 14 be attached to the stent element 12 in such a way that the device does not become significantly less flexible and the device does not have significantly more material added to it. Although attaching the cover using a ribbon of adhered film can produce acceptable results, it is not believed to be preferred since the film may increase the rigidity of the device, impart undesirable undulations or corrugations to the luminal surface during bonding, and the film also adds volume to the device. Accordingly, the preferred attachment method for joining the stent element 12 and the cover 14 is to apply layers of the cover to both the inside and outside of the stent frame, then bonding the layers together at a temperature above the crystalline melt temperature of PTFE (327° C.). The luminal surface is preferably formed to be as smooth as possible (i.e., a smooth surface devoid of as much corrugation as possible). Alternatively, attachment may be performed by coating the stent frame with an adhesive or applying an adhesive to the cover material, then bonding the cover to the frame. One suitable adhesive material for these applications is fluorinated ethylene propylene (FEP).

The stent element 12 is preferably formed from a super elastic material that will withstand extreme compaction yet will readily return to its original dimensions without damage when unconstrained. Additionally, if the stent element 12 is formed from a material that will self-expand in place, maximum compaction can be achieved since a means of dilatation or expansion (e.g., employing a balloon catheter) need not be delivered within the device in its compacted dimensions. Suitable materials include alloys of stainless steel, nickel-titanium alloys (nitinol), tantalum, platinum, and titanium and rigid polymers.

The preferred material comprises a nickel-titanium alloy (nitinol) metal wire having a diameter of about 0.4 mm or less, and more preferably, a diameter of about 0.2 mm or less. For extremely small stent-grafts, a wire with a diameter of about 0.1 mm or less may be preferred. The preferred nitinol wire comprises a nickel content of about 51% and a titanium content of about 49% (for example, SE 508 nitinol wire available from Nitinol Devices & Components, Fremont, Calif., USA). Additional properties that the wire may beneficially have include: a tensile strength of about 1200 MPa or more; cold working of about 40–45%; a tensile modulus of approximately 35 to $70 \times 10^6$ kPa; and an electropolished finish.

A self-expanding stent element may be formed from this material using a pin-jig and following conventional procedures, such as those taught in PCT Application PCT/US96/19669 to Martin et al., incorporated herein by reference. The preferred cross-sectional shape of the stent structure is not necessarily circular. It is possible that wire having an oval-shaped cross-section or a nitinol ribbon may be configured into an acceptable device. Likewise, with laser-cut tubes, there is a great deal of flexibility with cutting and polishing to achieve non-circular cross-sectional geometries.

Since the elastic properties of the stent material, the moment of inertia of stent cross-sectional geometry and the design of the overall stent structure combine to dictate the physical characteristics of the stent, the specific strut material, cross-sectional geometry, and stent design may be integrally linked to given clinical applications.

By forming a device using the preferred materials of about 0.003 mm thick expanded PTFE membrane and about 0.3 mm diameter nitinol metal wire that are adhered together by heat bonding, a 40 mm diameter thoracic aortic stent-graft device, as shown in FIG. 1, can be readily compacted down to a 3.33 mm or less diameter delivery profile, as shown in FIG. 2. As is explained in greater detail below, even further profile reduction can be achieved by employing unique folding and restraining advances of the present invention.

Figure 3:
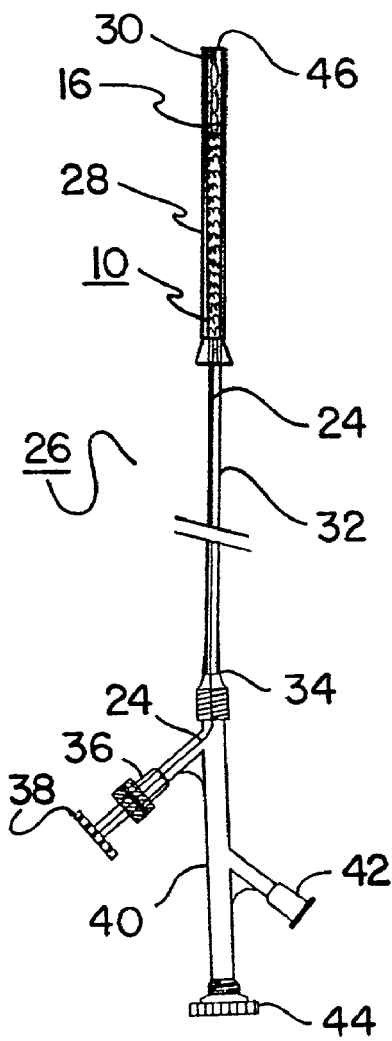
FIG. 3 is a side elevation view of one embodiment of deployment apparatus for use with the present invention.

A delivery apparatus that may be used to deliver an endoprosthesis 10 of the present invention is illustrated in FIG. 3. This deployment apparatus 26 comprises: an introducer sleeve 28; a restraining device 16; a distal shaft 30; a proximal shaft 32; a strain relief 34; a deployment port 36; a deployment knob 38 mounted within the deployment port 36 that is connected to a deployment line 24 attached to a restraining device 16 surrounding the endoprosthesis 10; a side arm adapter 40; a flushing port 42; and a guidewire port 44. A radiopaque marker 46 may be provided on the distal shaft 30 to aid in the remote positioning of the endoprosthesis 10. The operation of the deployment apparatus 26 is explained in detail below with reference to FIGS. 10 through 13.

Low profile delivery of a bifurcated device, such as that employed in repairing an abdominal aortic aneurysm (AAA), is an even more challenging application of the present invention. The challenge in these applications is that an aneurysm will commonly form at the junction of the common iliac arteries in the abdominal aorta. In order to repair this defect, a device ideally comprises a bifurcated structure that has one large opening at one (proximal) end that splits into two smaller legs at the other (distal) end. In this manner, the device can attach to the host artery above the aneurysm and below the aneurysm in each of the iliac arteries individually, thereby excluding the aneurysmal lesion from the blood stream.

Although a bifurcated device is preferred for treating AAA, such devices have a number of inherent problems. First, the fact that a bifurcated device has two legs presents a placement problem when the device is to be delivered by way of one of the iliac arteries. While the upper proximal end and one leg can be easily positioned properly around the aneurysm, the ability to then direct the other leg through the other iliac artery can be a challenge for medical personnel. Second, the complexity of the bifurcated device necessarily adds a substantial amount of bulk to the device when compacted.

Numerous proposals have been made to address the first of these problems. One common approach is illustrated in FIGS. 4 through 6. In this embodiment, a bifurcated endoprosthesis 48 is provided that includes a trunk segment 50 having a long ipsilateral leg 52 and a short contralateral leg 54. The trunk segment 50 is delivered through the ipsilateral iliac artery and positioned and deployed in place.

A separate contralateral leg stent-graft segment 56 is then delivered through the contralateral iliac artery and deployed to join to the short contralateral leg 54 on the trunk segment 50 to complete the bifurcated device 48. The completed device is illustrated in FIG. 6.

Even with separation of the bifurcated device into two separately deployable segments 50, 56, the trunk segment 50 cannot be compacted into small enough dimensions for percutaneous delivery (although the contralateral leg segment 56 typically can be compacted using conventional methods from deployed dimensions of about 8 to 16 mm in diameter down to compacted dimensions of about 4 to 5 mm in diameter). Typically the trunk segment 50 will have a deployed large proximal opening 58 measuring about 20 to 36 mm in diameter ("a") and a small distal opening 60 on the ipsilateral leg 52 measuring about 8 to 16 mm in diameter. Currently, this trunk segment 50 is delivered at a diameter of about 18 F (6.0 mm)—entirely too large for percutaneous delivery.

However, the device 48 may be constructed from a stent frame 62 employing the 0.3 mm nitinol wire previously described, with a cover 64 constructed from the 0.003 mm thick expanded PTFE membrane previously described. Joining the stent frame and cover together via heat bonding produces a low profile stent-graft of the present invention. Employing the low profile materials previously described, the trunk segment 50, having a proximal opening 58 of about 31 mm in diameter and a distal opening 60 of about 13 mm in diameter, can be reduced to a compacted dimension of 10 F (3.33 mm) or less. The total cover thickness, formed from multiple film layers, is preferably less than about 0.02 mm and more preferably about 0.013 mm or less.

Figures 7, 8:
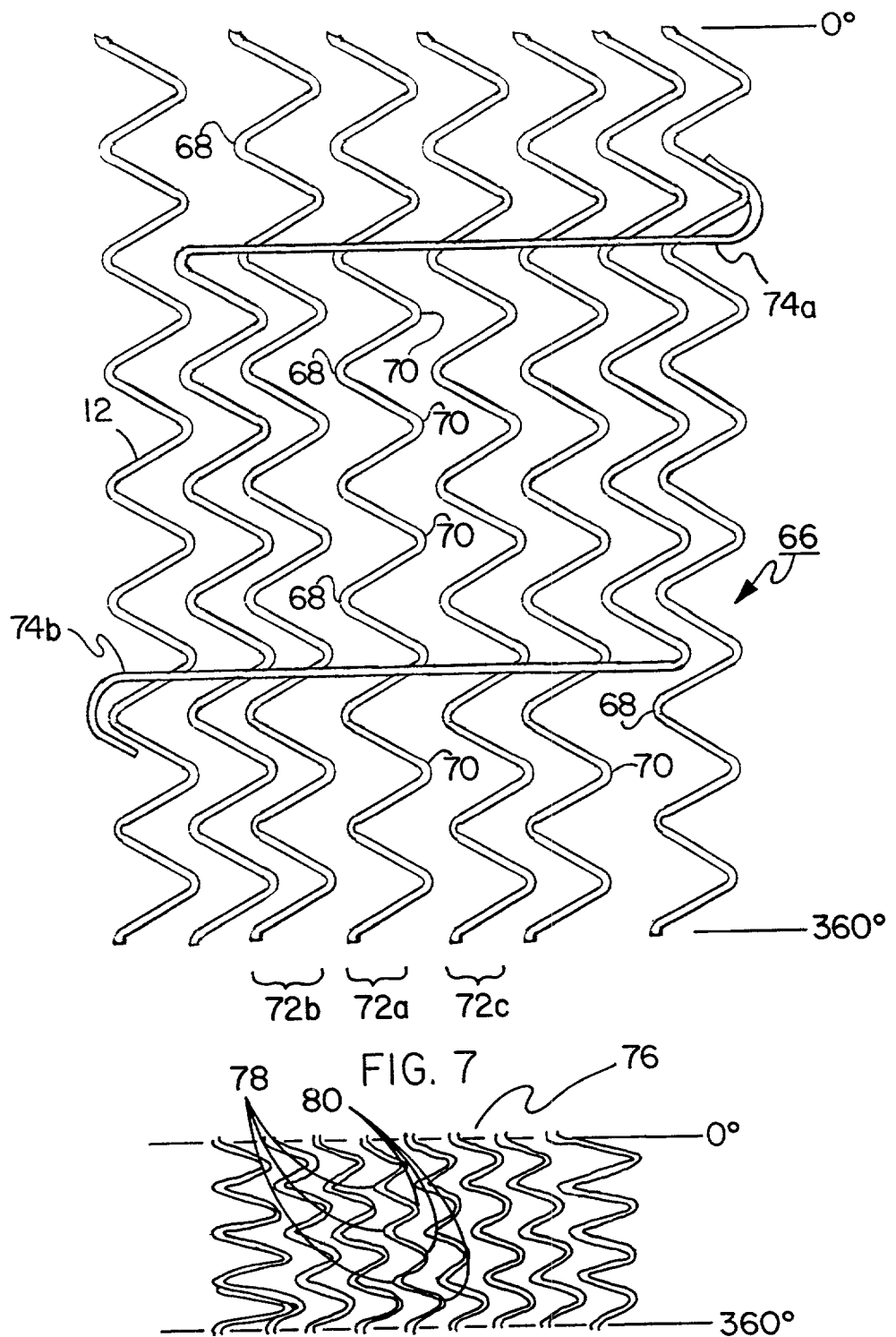
FIG. 7 is a top plan view of a stent pattern used in a thoracic aortic stent-graft shown in FIG. 1. The stent-graft is cylindrical but is represented in this "flat plan configuration" by making a longitudinal cut along the length of the endoprosthesis and the uncoiling of the endoprosthesis along this cut into a flat sheet.
FIG. 8 is a flat pattern configuration of the stent element that may be used to form a straight stent-graft of the present invention.
Figure 9:
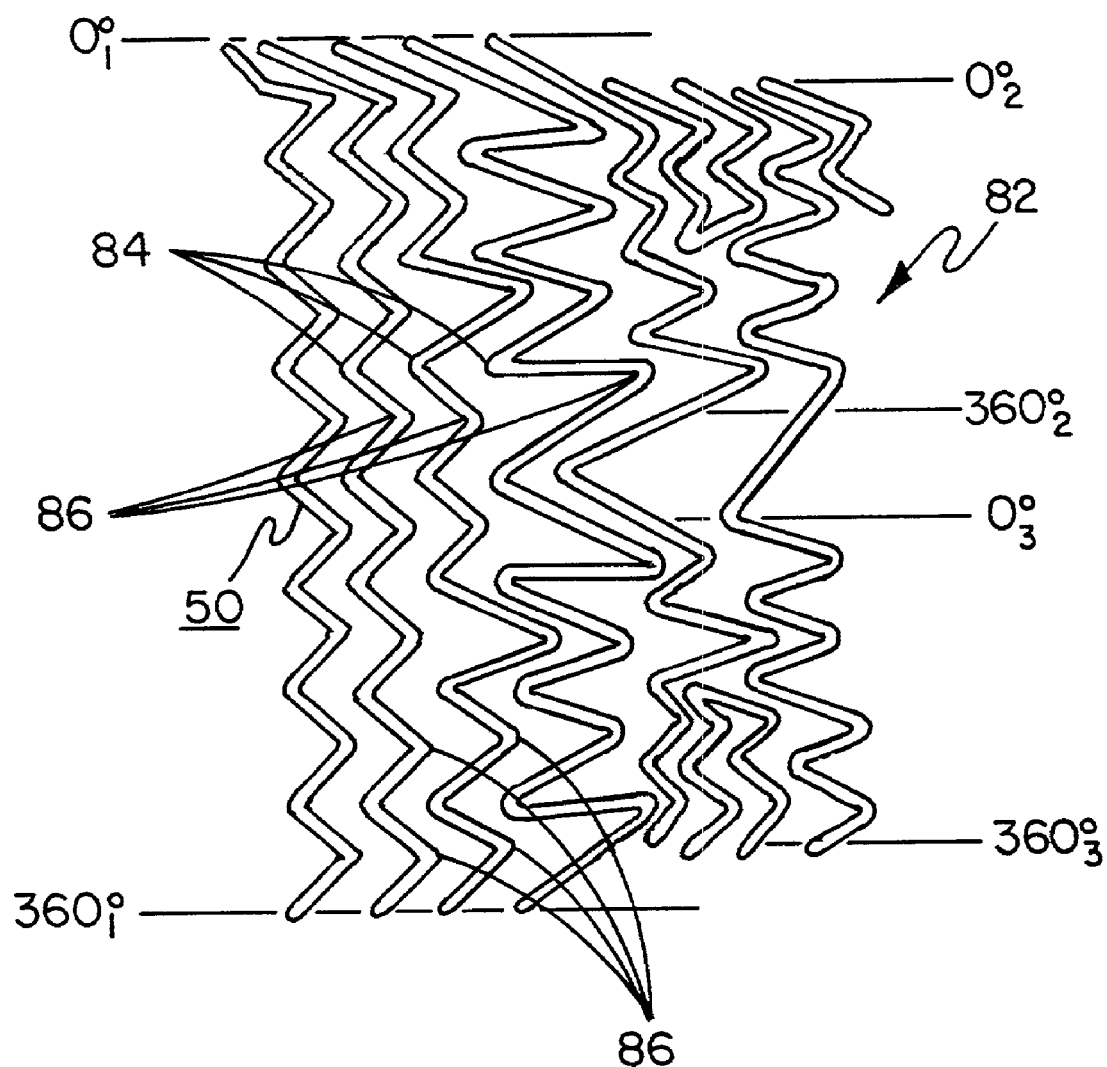
FIG. 9 is a flat pattern configuration of the stent element used to form the trunk component of the modular bifurcated stent-graft of FIGS. 4 through 6.

The preferred winding patterns for the various stent elements of the present invention are illustrated in FIGS. 7 through 9. FIG. 7 illustrates (in flat orientation) a winding pattern 66 for a thoracic aortic endoprosthesis shown in FIG. 1. In this instance the stent element 12 comprises an undulated wire having a series of forward facing apices 68 and rearward facing apices 70. As will be appreciated following review of the compaction techniques discussed below, it is preferred that the apices 68, 70 of each row are in phase with the apices in neighboring rows. For instance, the forward facing apices 68 in row 72a are directly in phase with the forward facing apices 68 of rows 72b and 72c. This winding pattern includes two longitudinal struts 74a, 74b to aid in maintaining the longitudinal length and column stiffness of the endoprosthesis.

FIG. 8 illustrates (again in flat orientation) a winding pattern 76 for a stent element used in a straight dimensioned endoprosthesis. Again, forward facing apices 78 and rearward facing apices 80 are in phase with neighboring forward and rearward facing apices.

FIG. 9 illustrates (again in flat orientation) a winding pattern 82 for the proximal end of the trunk segment 50 of the bifurcated graft shown in FIGS. 4 through 6. Again, within the constraints of this more complicated winding pattern, the forward facing apices 84 and rearward facing apices 86 are essentially in phase with neighboring forward and rearward facing apices.

While these winding patterns are preferred for the various described orientations, it should be appreciated that the exact pattern used may be application and material specific. Accordingly, the present invention is not intended to be limited to the winding patterns illustrated.

The process for deploying an endoprosthesis of the present invention is illustrated in FIGS. 10 through 13. In this instance a straight tube endoprosthesis, similar to the one illustrated in FIGS. 1 through 3, is being deployed in a vessel 88 having an aneurysm 90 therein.

Initially, a small incision is formed through the patient's skin at a site remote from the aneurysm, for instance to expose and access the femoral artery at the patient's groin. Using the deployment apparatus illustrated in FIG. 3, the delivery catheter 18 is passed through the patient's skin into the femoral artery via an indwelling introducer sheath. The introducer sheath is left in place through the skin and arterial wall to hold open this access site and provide a conduit into and out of the patient for insertion and withdrawal of the endoprostheses and other tools of the physician. Ultimately, it is the outer diameter of the introducer sheath that determines whether the procedure can be performed percutaneously. Most commercially available introducer sheaths have a wall thickness of about 1 F (0.33 mm), adding about 2 F (0.67 mm) to the diameter of the access site. Accordingly, a 10 F compacted endoprosthesis will require about a 12 F access site for introduction using conventional introducer sheaths.

The endoprosthesis 10, confined in restraining device 16 and mounted on the delivery catheter shaft 18, can be negotiated through the various blood vessels until it is positioned within the aneurysm 90, as illustrated in FIG. 10. Positioning of the device 10 in the vessel 88 can be directed using a fluoroscope or similar device. Radiopaque marker 46 can be used to aid in precise positioning of the device.

Once properly positioned, the restraining device 16 can be removed by actuating deployment line 24. This will allow the self-expanding device 10 to progressively enlarge in place, as shown in FIGS. 11 and 12. Once the restraining device 16 is completely opened or removed, the endoprosthesis 10 will be fully deployed, completely spanning the aneurysm 90, as is illustrated in FIG. 13. The delivery catheter 18 can then be removed. At this stage the device 10 can be further enlarged using a balloon catheter (which may be used to assure proper anchorage and smooth any wrinkles that may have formed during deployment). Following any subsequent procedures, all tools and delivery apparatus, including the introducer sheath, are removed and the access site is sealed.

It is preferred to compact the endoprostheses of the present invention through a funnel-shaped tapered die 92, such as that illustrated in FIGS. 14 and 15. The die 92 has a large opening 94 at one end and an internal taper 96 leading to a much smaller opening 98 at the opposite end. Preferably the large opening 94 is sized to be larger than the deployed dimension of the endoprosthesis. The taper 96 is preferably set at an angle 100 of approximately 5 to 45°. The smaller opening should be approximately the final desired compacted dimension of the endoprosthesis. The process for compacting an endoprosthesis through such a die 94 is explained in greater detail below in reference to FIGS. 19 through 22.

Compacting through a smooth tapered die 92, such as that illustrated in FIGS. 14 and 15, provides very good results. However, compacting in this manner tends to produce random folds within the compacted device. Moreover, the orientation of the forward-facing and rearward-facing apices of the stent tends to be random and disorganized. The present inventors have determined that far more effective and extensive compaction can be achieved if the process of folding the endoprosthesis into its compacted dimension is more carefully controlled. In particular, it has been determined that optimal compaction of some endoprostheses can be achieved by folding into evenly spaced pleats.

FIGS. 16a through 16c illustrate a modified tapered die 102 that is designed to provide pleated folds into an endoprosthesis. This die 102 again includes a large opening 94 at one end and an internal taper 96, and a small opening 98 at its opposite end. However, in this die 102 a number of raised flutes (or ridges) 104 are provided within the tapered die separated by grooves 106. The raised flutes 104 and/or the grooves 106 may be formed by molding or machining the shapes into the die 102. Alternatively, as is illustrated, the flutes 104 may be formed by forming evenly spaced bands 108 wound around the tapered die 102, such as by using nylon filament with a diameter of about 0.38 mm. Regardless of how the flutes 104 are formed, each raised flute 104 preferably corresponds to one desired pleat to be formed in the endoprosthesis. Additionally, the flutes may be configured to be free-floating within the lumen of the tapered die so as to allow lateral movement of the flute as an endoprosthesis is drawn through it. This, for example, may be achieved by fixing the radial position of the flutes at the inlet to the die 94, but not restricting the radial position of the flute through the remainder of the die lumen. Alternatively, lines may be attached to the endoprosthesis prior to drawing and removed subsequent to compaction.

A stent or stent-graft is pulled through the tapered die by tying a series of tether lines around the circumference of the stent. When using a fluted, tapered die 102 precise pleat placement can be achieved by tying the tether lines to the portions of the stent that are to be folded outward. When pulled through the fluted, tapered die, the tether lines will self-align with the grooves in the die (thus folding outwardly) while the untethered portions of the stent will pass over the flutes (thus folding inwardly).

This process is illustrated in the single stent ring 110 being drawn through the tapered die 102 by tether lines 112 in FIG. 16c. As can be seen, the tether lines 112 have aligned with grooves 106, folding the stent ring 110 outwardly, while the untethered portions of the stent ring 110 are drawn over the flutes 104 and are being folded inwardly.

Figures 17A, 17B:
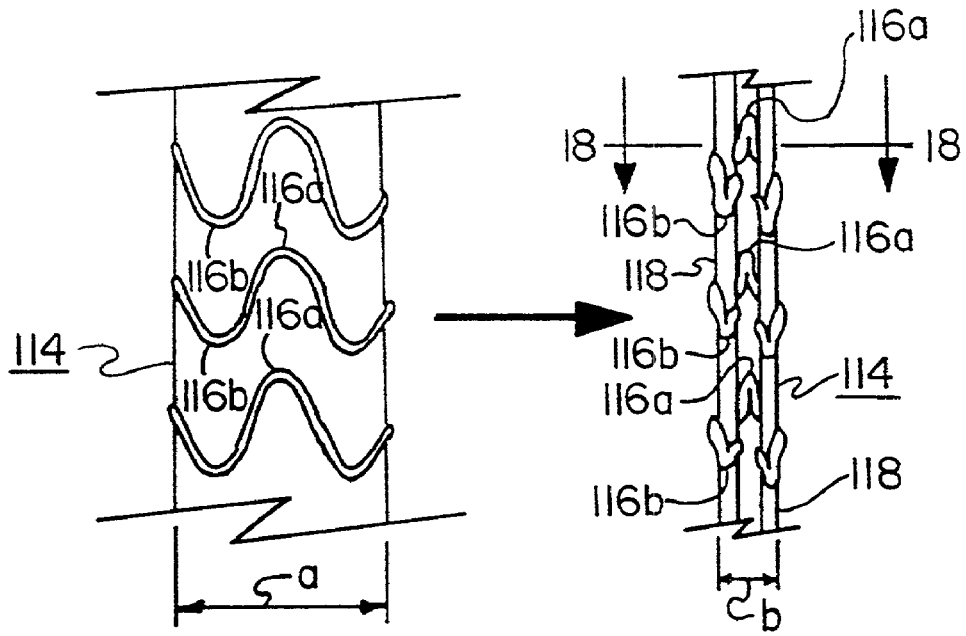
FIG. 17A is a side elevation view of a segment of a straight stent-graft of the present invention shown in its fully deployed dimension.
FIG. 17B is a side elevation view of the segment of straight stent-graft of FIG. 17A shown in its compacted dimension having been folded into pleats.
Figure 18:
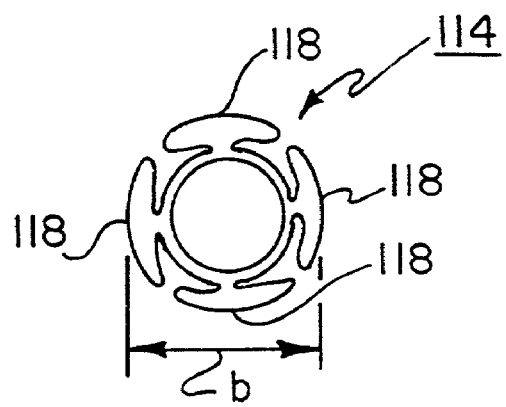
FIG. 18 is a section view of the pleated stent-graft of FIG. 17B along section line 18—18.

As is illustrated in FIGS. 17A, 17B, and 18, a stent-graft implantable device 114 formed in this manner will pass from a deployed dimension "a" to a pleated compacted dimension "b." Since the tether lines can direct where the folds will occur, this folding technique can be used to direct all of the forward facing apices 116a in the stent frame to fold inwardly. In the folded orientation of FIG. 17B, all the forward facing apices 116a have been folded beneath the outer surface of the compacted device while the rearward facing apices 116b have been folded to the outer surface of the compacted device into pleats 118. This kind of control of folding is believed to be very beneficial to maximize folding efficiencies by increasing the density of the compacted endoprosthesis. Additionally, it has been found that it is sometimes beneficial to have exposed apices of a stent all facing in only one direction (that is, only the rearward facing apices 116b are exposed in FIG. 17B). In this way, the folded device is less likely to catch on biological structures (such as plaque and side branches), restraining sleeves, deployment lines, and other devices that may be pulled over the compacted stent.

The advantage of forming a stent frame with all of the forward and rearward facing apices in phase with one another should now be evident from the above description. By keeping the apices in phase, pleats can be formed that will direct all of the apices of one orientation into or out of the compacted devices. Additionally, by employing in-phase apices, greater compaction is achievable (since all of the apices will fold and compact in the same direction).

It should be appreciated that the pleated folding methods described herein can be used to direct apices into a wide variety of folded patterns. As such, the terms "forward" and "rearward" facing apices are used only for convenience to describe sets of apices that face in one direction or an opposite direction, without regard to the actual direction the device may ultimately be deployed.

Figure 19:
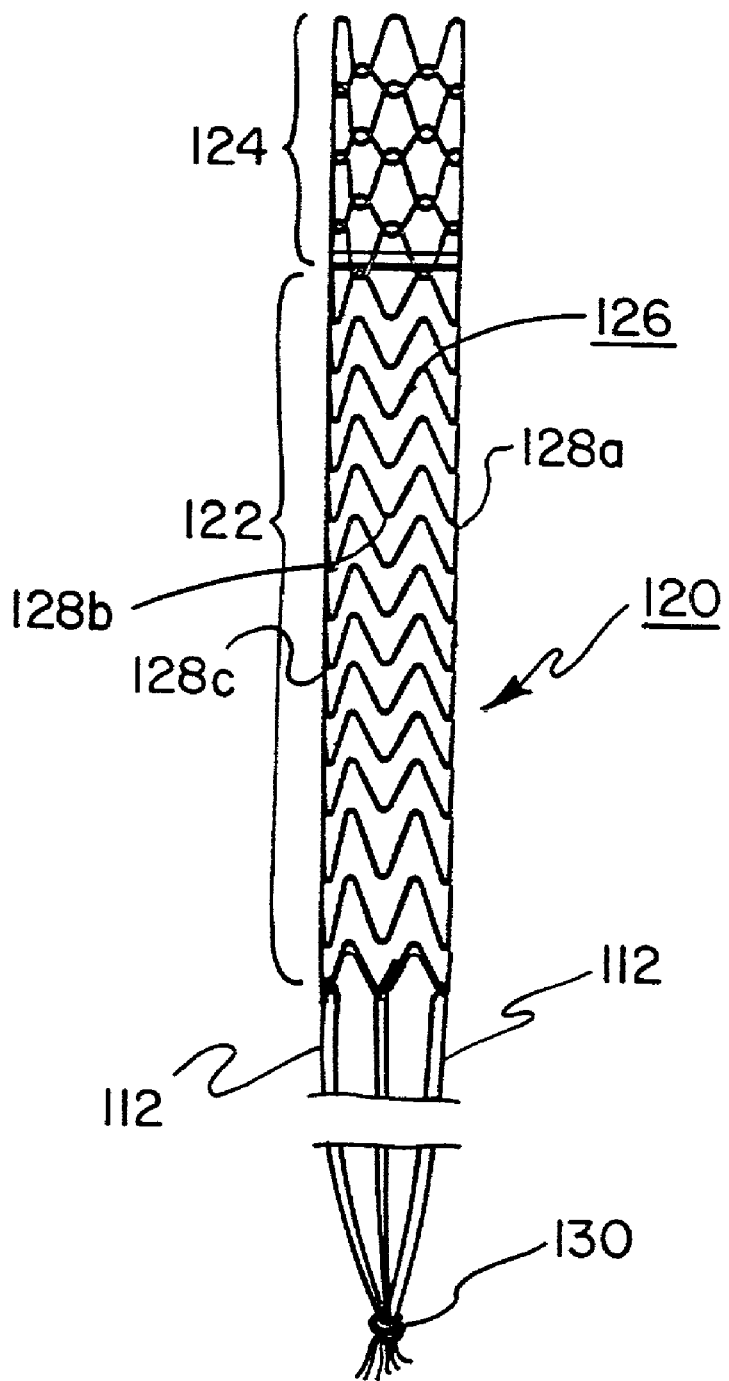
FIG. 19 is a side elevation view of a partially covered stent-graft of the present invention in a fully deployed dimension having tether lines attached to it for compaction through a tapered die, the tether lines being aligned with stent undulations all facing in the same direction.

FIG. 19 illustrates a partially covered stent-graft 120 being prepared for compacting through a tapered die. In this instance the stent-graft 120 comprises a device with covered segment 122 and an uncovered segment 124. The tether lines 112 are attached to either end of the stent frame 126 in an evenly spaced manner. In this instance the tether lines 112 are aligned with rearward facing apices 128a, 128b, 128c (which are intended to remain exposed). The tether lines 112 may be formed from thin wires, polymer fibers, or other suitable materials. The tether lines 112 are joined together to form a termination such as a knot (or cuff) 130.

Figure 20:
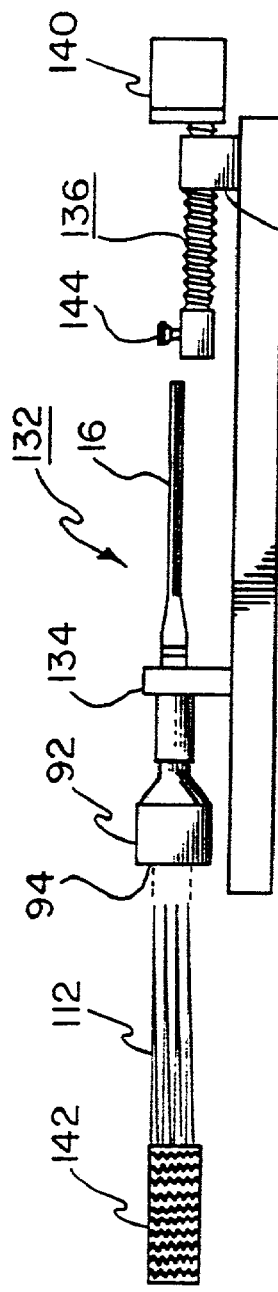
FIGS. 20 through 22 are side elevation views of a compression fixture used to compact a stent-graft of the present invention through a tapered die and into a restraining sleeve, a straight stent-graft of the present invention being illustrated in the sequential compaction steps.
Figure 21:
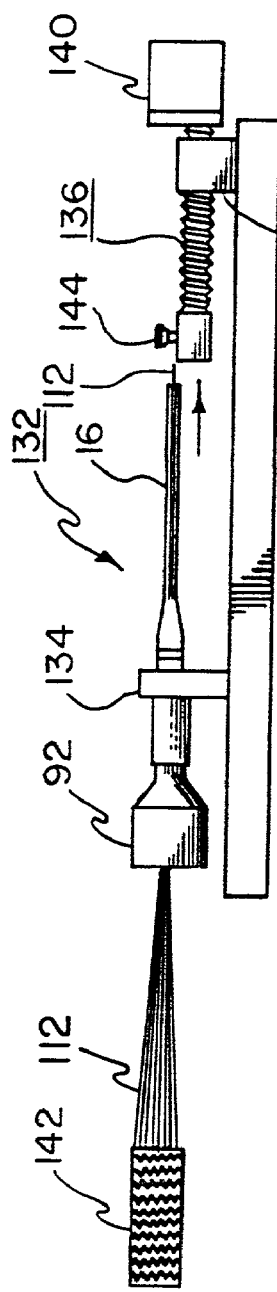
Figure 22:
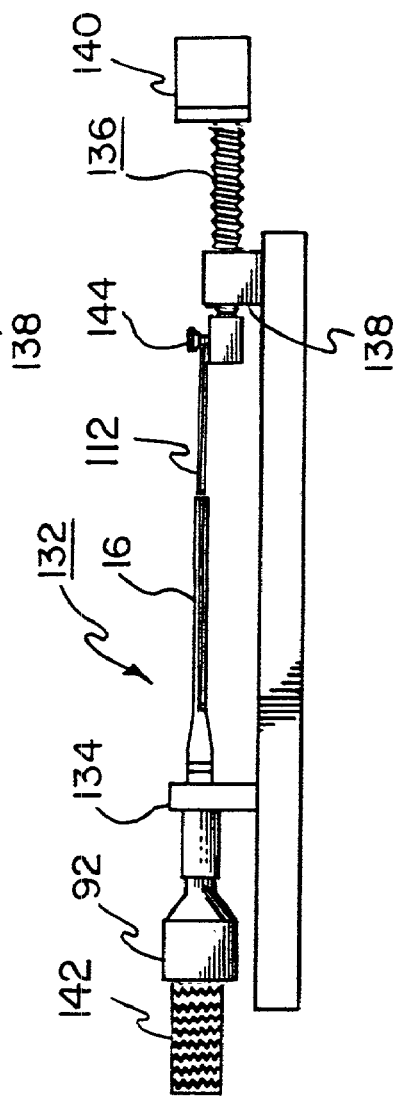

One apparatus 132 suitable for compacting endoprostheses through a tapered die is illustrated in FIGS. 20 through 22. The apparatus 132 comprises a jig 134 for holding a tapered die 92 and a restraining device 16, and an actuation mechanism 136, in this example a screw drive 138 actuated by a motor 140.

A stent or stent-graft device 142, with tether lines 112 attached, is then oriented by large opening 94. Tether lines 112 are then passed through the die 92 and the restraining device 16, and attached to the actuation mechanism 136 at post 144, as is shown in FIG. 21. Once attached, the actuation mechanism is used to draw the stent-graft 142 through the tapered die 94 and into the restraining device 16 using a constant rate of translation, or, alternatively, a constant tensile force applied to the tether lines. The device is preferably pulled through the die at a low rate, such as 200 mm/min or slower. After the stent-graft device 142 has been compacted into the restraining device 16, the tether lines 112 can be removed and the compacted device can then be mounted on a catheter and otherwise packaged and prepared for delivery. Alternatively, the device can be compacted directly onto a catheter.

It has been found that significantly smaller compacted dimensions can be achieved if the endoprosthesis undergoes repeated compressions through a series of progressively smaller tapered dies. It is believed that an additional reduction in compacted size can be achieved simply by passing the endoprosthesis through a series of 2 or more, preferably 3 to 6, tapered dies of progressively smaller dimensions. As long as excessive compaction is not attempted, this process does not appear to damage the endoprostheses. Drawing the endoprosthesis repeatedly through a same-sized die can also enable the device to be subsequently drawn through an even smaller die. This technique can reduce the profile by 1 to 2 F or more.

The restraining device 16 used to contain the self-expanding endoprostheses of the present invention may also be reduced in profile to aid in reducing the ultimate compacted dimension of the present invention. With respect to the membrane restraining device previously discussed and illustrated in FIG. 2, the overall thickness of the membrane may be reduced to its absolute minimum dimensions. For example, the preferred restraining means will have a thickness of 0.07 mm or less, and more preferably 0.025 mm or less.

Figure 23:
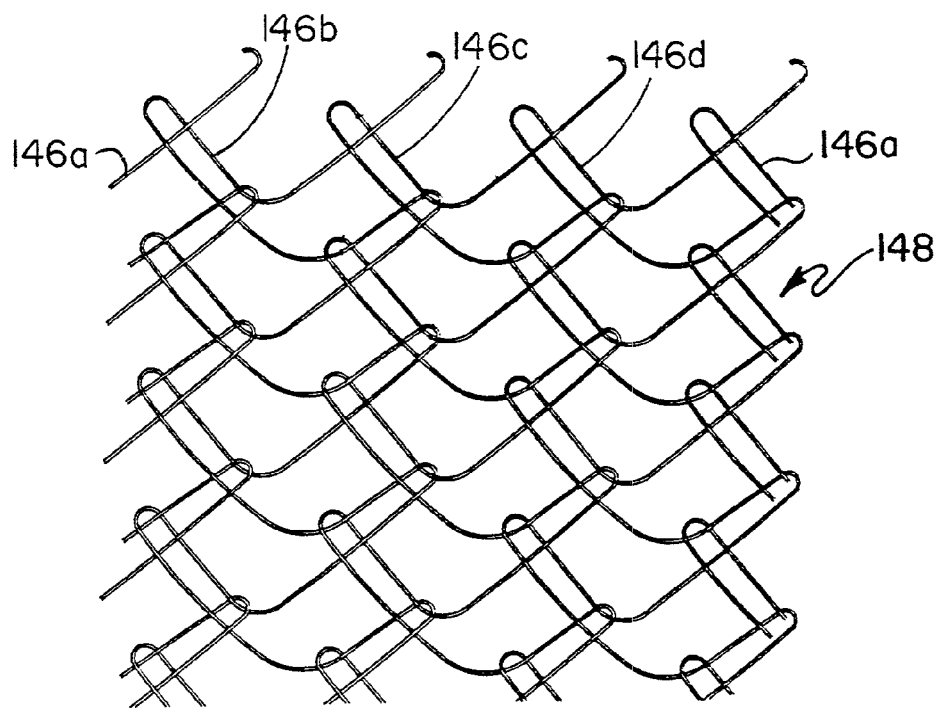
FIG. 23 is a flat pattern configuration of another embodiment of a restraining sleeve used to constrain the stent-graft of the present invention.
Figure 24:
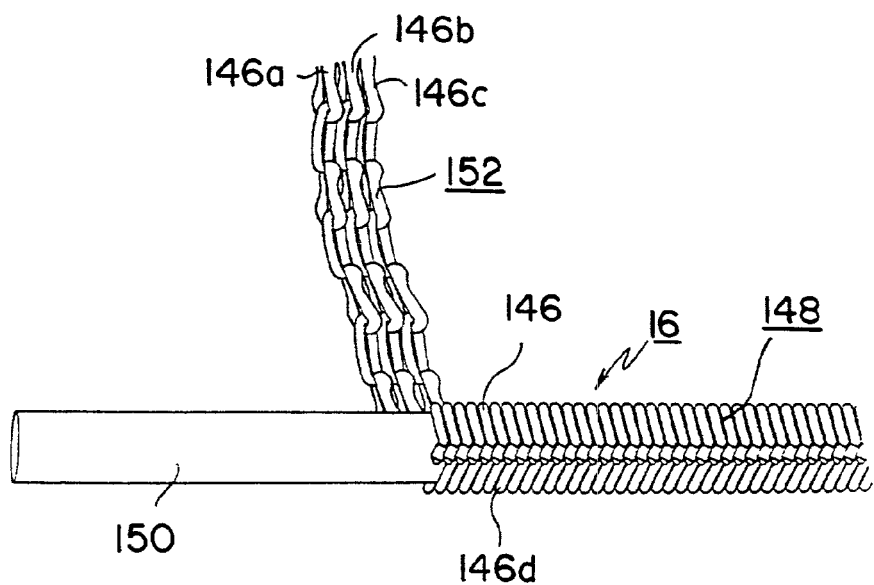
FIG. 24 is side elevation view of a restraining sleeve incorporating the pattern of FIG. 23, with the sleeve shown partially removed via an integral, multi-filament deployment line.

Another approach is to employ a releasable thread as the restraining device 16. For instance, FIGS. 23 and 24 illustrate a series of threads 146a, 146b, 146c, and 146d that are formed into a warp knit 148 around a device 150. This form of containment device is disclosed in U.S. patent application Ser. No. 09/098,103, filed Jun. 15, 1998, to Armstrong et al., incorporated herein by reference. By releasing one thread of the warp knit 148 at one end of the device (for example, thread 146a), the entire restraining device will unravel and separate as a cohesive deployment line 152, as is shown in FIG. 24. This form of restraining device has proven very effective at both containing a self-expanding stent element and releasing it as an entire unit. Moreover, this form of restraining device adds minimal profile to the compacted device. Although not preferred, another device employing threads to contain an endoprosthesis with minimal profile increase is disclosed in U.S. Pat. No. 5,405,378 to Strecker, also incorporated by reference.

Figure 25:
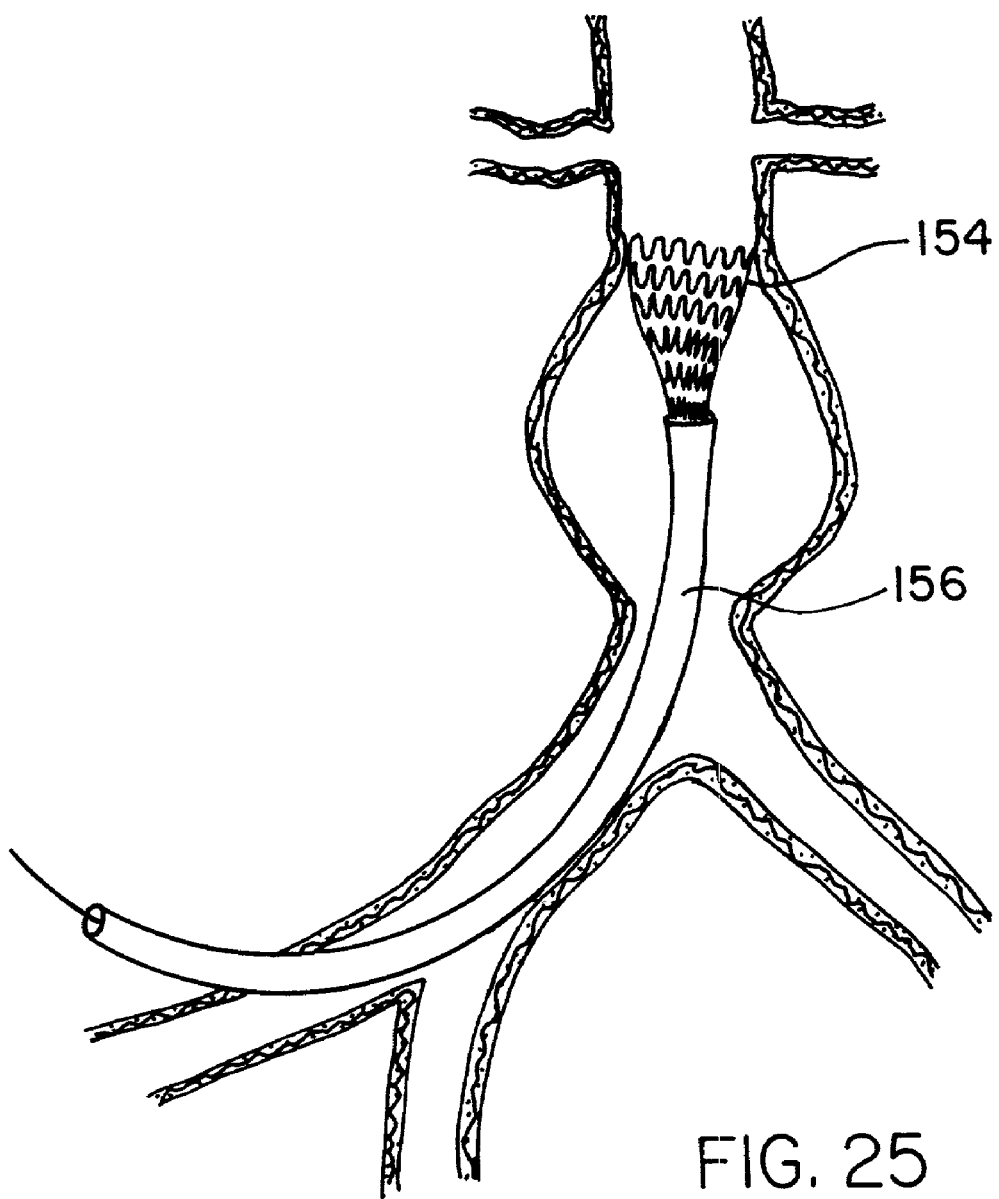
FIG. 25 is a side elevation view of another embodiment of a stent-graft of the present invention being deployed in an aneurysmal, bifurcated blood vessel shown in cross-section.
Figure 26:
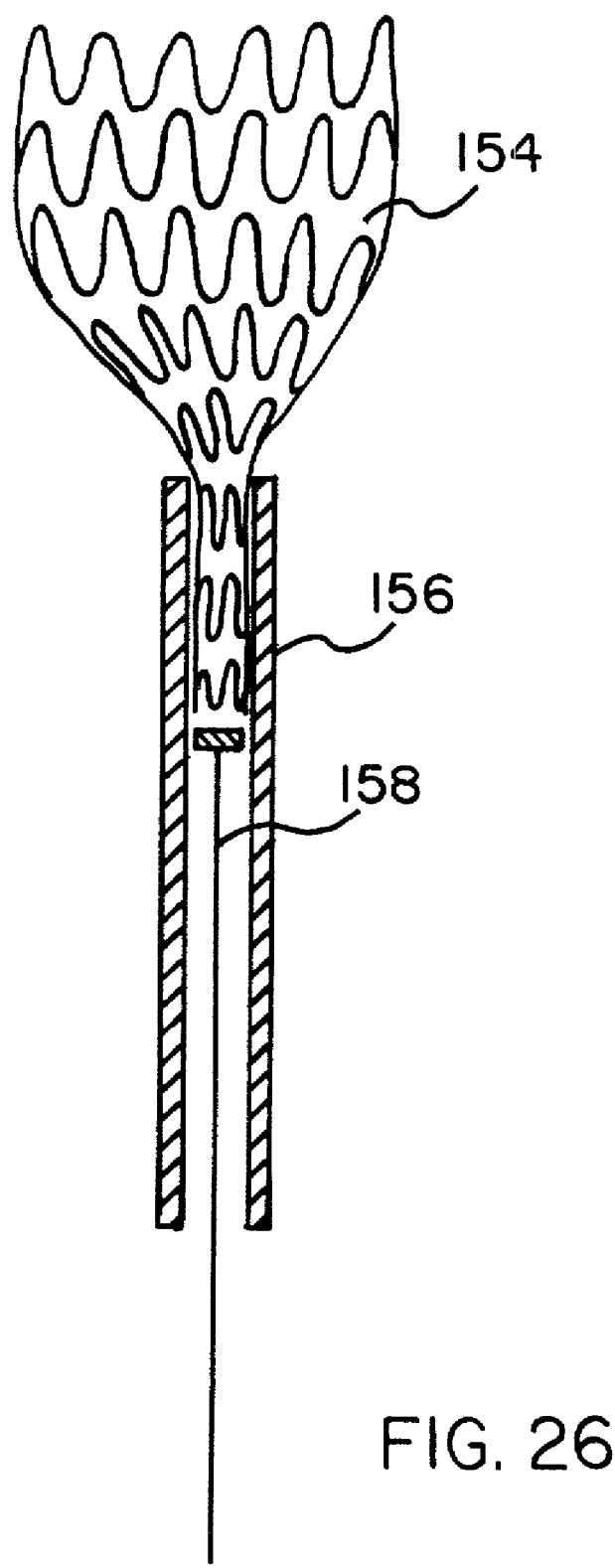
FIG. 26 is longitudinal cross-section view of the stent-graft embodiment shown in FIG. 25 illustrating a pusher mechanism for stent-graft deployment directly from a delivery catheter without use of a guidewire or a separate restraining sleeve on the stent-graft.
Figure 27:
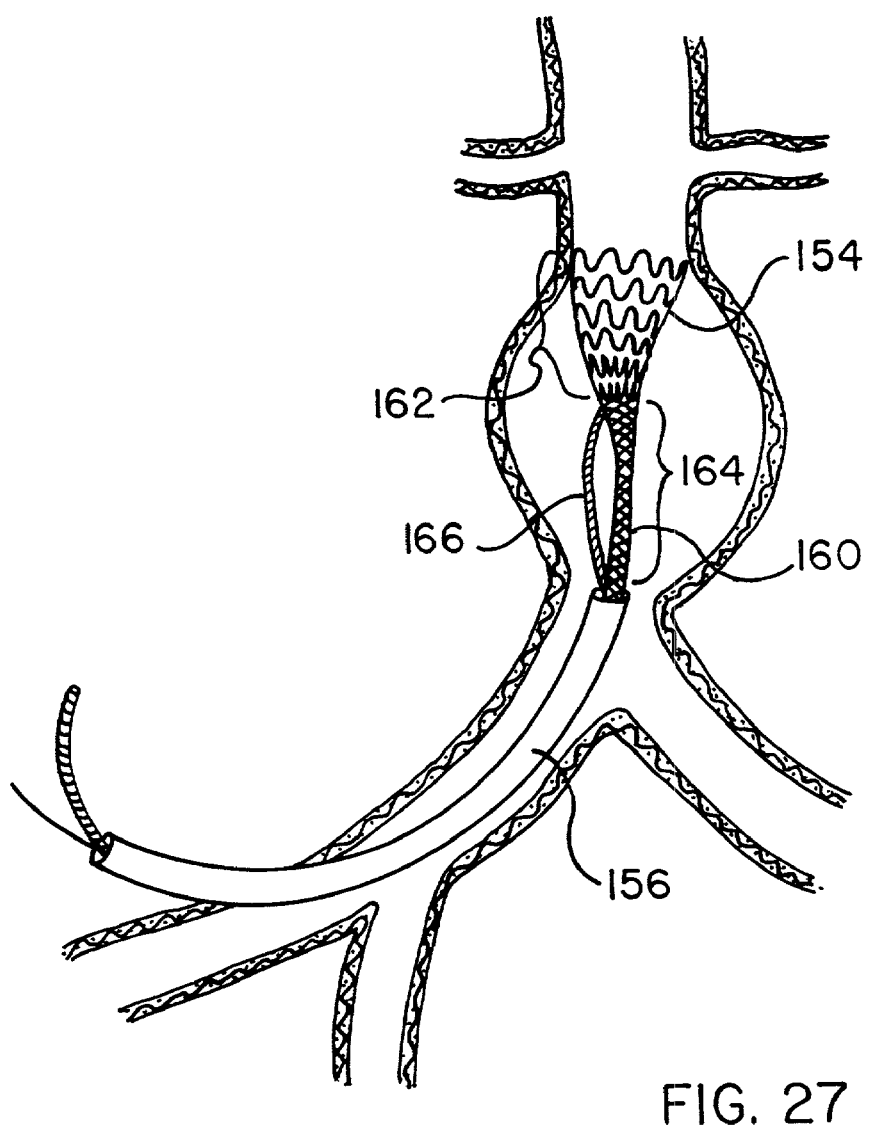
FIG. 27 is a side elevation view of another embodiment of a stent-graft of the present invention being deployed in an aneurysmal, bifurcated blood vessel shown in cross-section.

Still another embodiment of a device for containing the compacted stent is illustrated in FIGS. 25 through 27. When deploying therapeutic devices into the vessels of the human body conventional techniques entail starting the procedure with a standard guidewire to traverse tortuous bends and or obstructions. Once the guidewire is directed to the desired destination in the vessel, a catheter such as a guiding catheter or introducer sheath is coaxially inserted over the guidewire and advanced to the treatment site. At this point in the procedure, as depicted in FIG. 25, the clinician could remove the guidewire and deploy a device through the catheter, advance a device delivery catheter through the indwelling catheter or replace the initial guidewire with a smaller guidewire. The smaller guidewire is frequently used in order to traverse a small vessel side branch or obstructive lesion and deliver therapeutic devices. The use of smaller guidewires has the added benefit of allowing the use of even lower profile devices since the lumen of the stent or stent-graft can be reduced further during packing.

It is maintained that even smaller profile devices can be introduced should the need for a guidewire be obviated. Such is the case should the following procedure be followed: introduce a guidewire past the site to be treated, coaxially position a long introducer sheath or catheter to the end of the guidewire, remove the guidewire, advance the compacted stent or stent-graft beyond the end of the introducer sheath by pushing it with means such as a wire, and deploy the stent or stent-graft. This procedure affords the ability to compact stents or stent-grafts to the extent that no appreciable lumen exists in the compacted state. This further reduction in profile, although minimal, can be enough to convert a surgical procedure to a percutaneous procedure.

One device allowing for such a procedure is illustrated in FIGS. 25 and 26. In this embodiment an endoprosthesis 154 is compacted directly into a long introducer sheath 156, with the introducer sheath 156 serving both as a means of directing the endoprosthesis to the treatment site and as the restraining device used to hold the endoprosthesis in its compacted dimension until deployment. As is shown in FIG. 26, a pusher mechanism 158 may be directed through the introducer sheath 156 to push the endoprosthesis out of the tube and deploy it in place. This form of deployment apparatus can save significant compacted profile by eliminating the need for a guidewire and/or a separate restraining sleeve on the stent or stent-graft.

FIG. 27 demonstrates that the same constraint mechanism shown in FIGS. 25 and 26 can be combined with other restraining devices 160, such as the knitted restraining device illustrated in FIGS. 23 and 24, to provide for delivery in distinct phases. In this instance a first segment 162 of the endoprosthesis 154 deploys when pushed from the introducer sheath 156 while a second segment 164 remains contained by restraining device 160. Restraining device 160 can be separately removed when desired by actuating deployment line 166.

By way of summary, the present invention employs a series of techniques that combine to reduce the delivery profiles of stent-graft devices. These techniques include:

Thin, Strong Coverings:

Thin, strong expanded PTFE and/or polyester materials are employed to reduce the mass and volume of the stent covering. In the case of the use of expanded PTFE films, the profile is significantly reduced by creating a circumferentially and longitudinally strong cover by applying very high strength films directly to the stent frame. Other thin, strong biomaterials may also be used in the present invention, including but not limited to fluoropolymer elastomeric materials and polyurethanes.

Thin, Strong Stent Frames (Wires and Cut Frames):

Nitinol is used because of its superior strength, super elasticity, and biocompatibilty. Alternative materials including, but not limited to, tantalum, titanium and stainless steel may also be used.

High Packing Efficiency Stent Frame Design:

Nitinol wire stent-frames are formed utilizing a construction that enables a very high degree of compaction because of: nesting of in-phase apices; sliding of the apices over top of one another upon compaction to ease the compaction process; and facilitating folding efficiency of the material.

Improved Method of Attaching Cover Material to Stent Frame:

Bonding of the graft covering to the stent is accomplished using as little additional material as possible. In many cases, the expanded PTFE material is simply heat bonded together. For examples in which the stent frame is covered with, but not encapsulated by, expanded PTFE material, the stent frame is first prepared by applying a very thin coating of FEP powder. Other bonding techniques may employ coating the stent frame by dipping it in FEP dispersion, using expanded PTFE film containing either a continuous or discontinuous layer of FEP, or using another suitable bonding agent.

Improved Stent-graft Packing Techniques:

For a given stent-graft design, it was unexpectedly learned that repeated pulls of the devices through the same sized smooth dies enabled a further reduction in compacted profile. Furthermore, a fluted tapered die enables even greater compaction by producing an efficient stent-graft folding pattern.

Low Profile Restraining Methods:

The delivery profile is further reduced by drawing down a delivery tube to obtain a strong, thin-walled means of restraining the stent-graft in the compacted state. Alternatively, a delivery tube constructed from knitted threads that unravel when pulled from a line extending outside the body can be used as a low profile restraining cover.

Delivery Techniques:

Delivery techniques, such as using an introducer sheath and a pusher mechanism, can be employed to further reduce the profile of compacted devices to be introduced.

Individually, each of these techniques results in a measurable decrease in profile when applied to stent-grafts. The combination of these properties provides dramatic improvements in delivery profiles. Referring again to FIGS. 1 and 2, an endoprosthesis of the present invention having a deployed dimension of "a" in cross-section diameter and a compacted dimension of "b" in cross-section diameter is capable of achieving dramatic ratios of expansion. For example, a conventional 40 mm aortic stent-graft with limited foreshortening might achieve a ratio of a:b of 3.5:1 to 5:1. By contrast, a 40 mm stent-graft endoprosthesis of the present invention can achieve ratios of a:b of at least 7:1 up through 8:1, 9:1, 10:1, 11:1, 12:1, 13:1 and 14:1 or more.

As has been explained, this can lead to a device that is capable of achieving a deployed dimension of 23 mm or more (and preferably 26, 28, 30, 32, 34, 36, 38, 40, 42 mm or more) in cross-sectional diameter that can be reduced to a compacted dimension of 12 F or less (and preferably less than 11 F, 10 F, 9 F, 8 F, 7 F, 6 F, or less).

As has further been explained, the compacting technology of the present invention also permits construction of extremely small devices, on the order of 4 mm or less in deployed diameter that can be delivered in a compacted dimension of less than 3 or 2 F (1 or 0.7 mm). These very small devices possess a:b ratios of 2:1, 3:1, 4:1, 4.5:1, and 5:1, or more.

Equally important the stent-grafts of the present invention achieve substantial compaction with minimal change in length between the enlarged deployed dimension and the compacted dimension. As a result, the device can be accurately positioned and deployed. Additionally, the lack of significant foreshortening of the stent element allows more preferred cover materials to be used, such as expanded PTFE and woven polyester, that are not capable of undergoing substantial elongation and contraction. As has been noted, the endoprostheses of the present invention should undergo less than a 25% change in longitudinal length between its compacted dimension and its deployed dimension. Progressively desirable the device will undergo less than a 20%, 15%, 10%, 5%, 4%, 3%, 2%, 1% or less change in longitudinal length between its fully compacted dimension and its fully deployed dimension.

The consistent length of the present invention is achieved through the combination of materials and structures defined herein. Among the highly effective methods of preventing elongation or foreshortening of the device during compaction or deployment are: to employ stent element patterns that will naturally resist change in longitudinal length when compacted; to use relatively inelastic cover material; and to employ longitudinal structural elements, such as struts 74 shown in FIG. 7 or longitudinally applied (relatively inelastic) tapes or similar structures, to resist longitudinal changes in device length.

Without intending to limit the scope of the present invention, the following examples illustrate how the present invention can be made and practiced:

EXAMPLE 1

A 40 mm inner diameter thoracic aortic stent-graft is created. The stent portion is built using 0.30 mm diameter, 40–45% cold worked NiTi (nitinol) wire (SE 508; Nitinol Devices & Components, Fremont, Calif.) formed using a mandrel with protruding pins. The stent is constructed using a single wire, creating an undulating, helical, tubular stent member by winding the wire on a pin fixture as described in the above-mentioned published PCT patent application. See FIGS. 7 through 9.

Once the wire is formed on the pin fixture, it is heat treated in a convection oven set at 450° C. for 15 minutes. After removal from the oven and quenching in a water bath, the wire frame is unwound from the fixture creating a freestanding tubular stent frame.

The stent cover is constructed from a strong, thin film. A suitable film comprises expanded PTFE (ePTFE) film made in accordance with the teachings of U.S. Pat. No. 5,476,589 to Bacino, incorporated by reference. This expanded PTFE "cover film" material is chosen for its biocompatibilty, strength, and thinness. The preferred material possesses a matrix tensile strength of about 900 MPa in its high strength (longitudinal) direction a thickness of about 0.003 mm, and a density of less than about 0.8 g/cc and more preferably between about 0.15 to 0.4 g/cc. Matrix tensile strength is determined with an INSTRON tensile testing machine, using pneumatic cord and yarn grip jaws, a 25.4 mm wide sample, a 102 mm jaw separation distance, and a crosshead speed of 200 mm/minute.

A 28 mm inner diameter ePTFE tube possessing a wall thickness of about 0.10 mm and a density of about 0.5 g/cc is stretched over a 40 mm outer diameter mandrel. This tube serves as a cushion to aid in the subsequent lamination of the ePTFE material to the stent frame and is not part of the final device. Suitable expanded PTFE tubes for this use are commercially available.

A "sacrificial film" is also used to facilitate the construction of the inventive device, serving as a release layer to aid in removal of the stent-graft from the cushion tube and mandrel and providing a radial force to aid in bonding the ePTFE to the stent. The sacrificial film is preferably one with high strength (or "retraction force") that will withstand the processing conditions. A suitable film is one made in accordance with U.S. Pat. No. 3,953,566, incorporated by reference, that has been sintered to maintain its dimensions during processing. This film is 25.4 mm and 50.8 mm wide, approximately 0.013 mm thick, and possesses a matrix tensile strength of about 690 MPa in its high strength (longitudinal) direction, tested as described above. It has a density of about 0.2–0.3 g/cc. This film is not a part of the final device. It should be noted that the PTFE films used in all the examples have all been subjected to temperatures exceeding the crystalline melt temperature of PTFE ("sintered"). One layer of this 25.4 mm wide film is helically wrapped on top of the cushion tube with about a 10% overlap, creating a continuous layer. The tail end of this film is left exposed at both ends of the mandrel.

Helical wrapping facilitates later removal of this film. This film layer is unraveled from under the device at the end of the process by pulling on this tail, in order to facilitate the removal of the stent-graft from the cushion tube and mandrel.

Next, two layers of cover film are applied in a cigarette wrap fashion such that the high strength direction of the film is oriented along the longitudinal axis of the tube, thereby creating a seam oriented along the entire length of the tube. One layer of the same cover film is then circumferentially applied. That is, the film is rolled on top of the previous layers such that the high strength direction of the film is oriented perpendicularly to the longitudinal axis of the tube. This procedure also produces a seam oriented along the entire length of the tube, but is not transferred to the luminal surface. The stent frame is then placed over the covered mandrel in such a way that the undulations are aligned in phase. Next, an additional circumferential layer of the cover film is applied, followed by two layers of the cover film applied longitudinally. Finally, eight layers of 50.8 mm wide film of the same type described above are applied in an up and back helical pattern. The cushion tube is secured to the mandrel with bands of wire to prevent longitudinal shrinkage during subsequent heating. The sequence of preparing the device and the number and orientation of film layers for this and other examples appear in Table 1. This table also describes properties of the stent-grafts.

TABLE 1

| | Example 1 | Example 3 | Example 4 | Example 6 |
|---|---|---|---|---|
| Deployed ID | 40 mm | 26 mm | 31 × 13 mm | 23 × 13 mm |
| Wire Diameter | 0.30 mm | 0.20 mm | 0.30 mm | 0.20 mm |
| Number of Apices | 8 | 8 | top of trunk: 8 leg: 4 | top of trunk: 8 leg: 4 |
| Stent Frame Treatment | 15 minutes @ 450° C. | 15 minutes @ 450° C. | 15 minutes @ 450° C. | 15 minutes @ 450° C. |
| FEP Heat Treatment | n/a | n/a | n/a | n/a |
| Cushion Tube/Mandrel | OD = 40 mm | OD = 26 mm | OD = 31 mm OD = 13 mm | OD = 31 mm OD = 13 mm |
| Inner Release Film | 1 layer | 1 layer | 1 layer | 1 layer |
| Inner Long. Film | 2 layers | 2 layers | 2 layers | 2 layers |
| Inner Circum. Film | 1 layer | 1 layer | 1 layer | 1 layer |
| Stent Frame | wire | wire | wire | wire |
| Outer Circum. Film | 1 layers | 1 layers | 1 layers | 1 layers |
| Outer Long. Film | 2 layers | 2 layers | 2 layers | 2 layers |
| Outer Comp. Film | yes | yes | yes | yes |
| Heat Bonding | 40 minutes @ 380° C. | 20 minutes @ 380° C. | 30 minutes @ 380° C. | 20 minutes @ 380° C. |
| Delivery Tube Dimensions (in mm) [ID/OD] | 10 F: 3.28/3.33 9 F: 2.92/3.00 | 6 F: 1.96/2.01 | 10 F: 3.28/3.33 9 F: 2.92/3.00 | 6 F: 1.96/2.01 |
| Guidewire Diameter/Delivery Profile | 0.89 mm/ 10 F no wire/ 9 F | 0.89 mm/ 6 F | 0.89 mm/ 10 F no wire/ 9 F | 0.89 mm/ 6 F |
| a:b Ratio | 12.2:1 13.7:1 | 13.3:1 | 9.5:1 10.6:1 | 11.7:1 |

Key: "n/a" indicates not applicable; "ID" indicates inner diameter; "OD" indicates outer diameter; "Number of apices" indicates the number of exposed apices at an end of a graft; "Long." indicates longitudinal; "Circum." indicates circumferential; "Comp." indicates compression; "Delivery profile" indicates smallest sized hole through which the compacted device plus delivery tube can fit; "a" indicates deployed dimension in mm; "b" indicates compacted dimension in mm.

The entire assembly is placed in an oven set to 380° C. for 40 minutes. The heat-induced retraction of the sacrificial film provides compressive bonding forces, thereby heat bonding the cover films, providing an integral stent-graft. The assembly is removed from the oven and allowed to cool. The eight outer layers of sacrificial film are removed, then the single inner layer the sacrificial film is removed. Next, the device and cushion tube are removed from the mandrel, and the stent-graft and cushion tube are separated.

Expanded PTFE sewing thread (RASTEX® Expanded PTFE Thread, 1200 denier, available from W. L. Gore & Associates, Inc., Elkton, Md.) is tied to one end of the device in order to facilitate pulling the device through a 30° included angle, polymeric, smooth, tapered fixture (funnel) in order to reduce the diameter. The device is successively pulled through longer funnels possessing the same inlet diameters (therefore, possessing smaller diameter outlets), thereby reducing its compacted diameter. The device is compacted to its minimum diameter using a fixture in which the small end of the funnel is mated with a capture tube that houses a thin-walled (approximately 0.025 to 0.038 mm wall thickness) polyester tube. This polyester tube is constructed by elongating a heated polyester shrink tube (item number 210100CST, available from Advanced Polymers, Inc., Salem, N.H.). The polyester tube is employed to maintain the stent-graft in the non-distended state and serve as a delivery housing tube for the stent-graft. The diametric reduction is facilitated by chilling the nitinol-based device with a refrigerant spray (Freeze Mist, G C Thorsen, Inc., Rockford, Ill.) during draw-down through the tapered die. The final constrained device plus polyester delivery tube fit through a 10 F hole. The thickness of the bonded ePTFE covering is approximately 0.013 mm. The device is pulled from the polyester tube. Upon release from the tube, the stent-graft is warmed to about physiologic body temperature (35–40° C.) to deploy it. The device is radially compressed once again after a 0.89 mm wire is inserted in the lumen of the device in order to simulate the presence of a guidewire. The use of the term "guidewire" in the examples and tables refers to such a spacer wire.

The device is once again captured inside a tube. The device plus a polyester constraining tube fit through a 10 F hole. Once deployed, the device self-expands in a 36° C. water bath to a 38 mm inner diameter. Gently pulling the stent-graft over a tapered mandrel increases its inner diameter to 40 mm. Note that blood pressure applies a radial force in vivo and self-expanding devices are typically subjected to balloon dilatation once they are deployed. (Note that the stent-grafts in all examples self-expand to the deployed diameters presented in Tables 1 and 2, unless otherwise noted.)

The graft is once more compacted without a guidewire. This time the delivered profile of the captured device is 9 F (that is, its dimension inside a delivery tube). The stent-graft deploys (self-expands) to a 39 mm inner diameter in a 40° C. water bath. Gently pulling it over a tapered mandrel increases its inner diameter to 40 mm.

The a:b ratio for this device ranges from 12.2:1 to 13.7:1 and increased with successive pull-downs.

Foreshortening is a percentage defined as the change in length from the captured state to the deployed state divided by the length of the device in the captured state, where the diameter of the device is at the minimum. The device is once again captured inside a 9F tube without a guidewire, as described above. The length of the device is measured in the captured state at 7.68 cm. The device is deployed in a 36° C. water bath. It deploys to a 40 mm. The length of the device is measured in the deployed state at 7.62 cm. The device foreshortened 1%.

EXAMPLE 2

Another 40 mm inner diameter thoracic aortic stent-graft is constructed using polyester as the stent covering material. The stent portion is constructed using 0.20 mm diameter nitinol wire (SE 508; 40–45% cold worked; Nitinol Devices & Components, Fremont, Calif.). Yellow polyester film (PES 30/25, available from Saatitech, Inc., Somers, N.Y.) is employed as the stent covering. The polyester material is approximately 0.046 mm thick. The stent member is formed and heat treated in the manner described above in Example 1. The stent covering is attached to the inner surface of the stent frame with CV-8 Sutures (available from W. L. Gore & Associates, Inc., Flagstaff, Ariz.), using a running stitch and tying the ends of the of the sutures together.

As in Example 1, the device is pulled down into a tapered fixture and contained within a capture tube containing a removable polyester inner liner. A 0.89 mm guidewire is inserted inside the stent-graft prior to compaction. A long tail of the polyester fabric material is used to pull the stent-graft through the fixture. The inner and outer diameters of the delivery tube are approximately 3.94 and 4.01 mm, respectively. The 40 mm stent-graft over a guidewire plus polyester tube (delivery tube) fit within a 12 F hole. The stent-graft deploys to 39 mm in a 36° C. water bath. It increases in inner diameter to 40 mm when gently pulled over a tapered mandrel.

The a:b ratio for this device is 10.2:1.

EXAMPLE 3

A 26 mm inner diameter thoracic aortic stent-graft is constructed using 0.20 mm nitinol wire (SE 508; 40–45% cold worked; Nitinol Devices & Components, Fremont, Calif.) and ePTFE film. This stent-graft is made in the same manner, with the same materials, as described in Example 1 following the steps outlined in Table 1. The device is drawn down over a 0.89 mm diameter wire to simulate the presence of a guidewire. The stent-graft and wire are pulled into a polyester tube (fabricated as described in Example 1). The stent-graft plus polyester tube fits within a 6 F hole. The stent-graft deploys to 24 mm in a 36° C. water bath. Gently pulling the stent-graft over a tapered mandrel deploys the device to 26 mm.

The a:b ratio for this device is 13.3:1.

EXAMPLE 4

The bifurcated stent-graft of the present invention consists of a modular design as described in PCT Application PCT/US98/27893 to Thornton et al., incorporated by reference. This design incorporates a main body (i.e., trunk) component that incorporates the trunk, one leg, and a portion of the contralateral leg, as is illustrated in FIG. 4. The contralateral leg constitutes the other component. These two components are independently introduced into the vessels. The contralateral leg is positioned inside the contralateral leg portion of the main body component. The geometry, hence volume, of the main body component mandates that its delivery profile is always larger than that of the leg component. Achieving a percutaneously deliverable main body component ensures that the entire device can be percutaneously delivered. Consequently, only main body components are constructed for the purposes of this and other bifurcated stent-graft examples.

The main body component of a 31 mm (trunk inner diameter) by 13 mm (limb inner diameters) bifurcated stent-graft designed for the treatment of abdominal aortic aneurysm disease is constructed using 0.30 mm nitinol wire and an expanded PTFE film. The stent portion is built using 0.30 mm diameter, 40–45% cold worked NiTi (nitinol) wire (SE 508; Nitinol Devices & Components, Fremont, Calif.) formed using a mandrel with protruding pins as previously described. The stent is constructed using a single wire, creating an undulating, helical, tubular, bifurcated stent member by winding the wire on a pin fixture as previously described. This pattern includes in-phase nested apices that aid in compaction.

With the exception of steps required to accommodate the bifurcated shape of the stent-graft, this stent-graft component is made in the same manner, with the same materials, as described in Example 1 following the steps outlined in Table 1.

The bifurcated section is constructed as follows. Y-shaped pin fixtures are used to construct the free standing stent frames and Y-shaped mandrel tooling is used to construct the stent-graft devices. As in other examples, a cushion tube is employed as a construction aid. One large ePTFE tube is sutured to two smaller ePTFE tubes to form a bifurcated cushion tube. Once placed on the mandrel the cushion tube is wrapped with sacrificial film with each leg of the construction wrapped individually and an additional layer covering the trunk. Subsequent layers of cover film are applied over the entire construction bridging over the gap between the individual legs of the bifurcation. The cover film covering the two legs is applied loosely to allow seam sealing of the cover film between the legs to form the smaller tubes of the bifurcation. The seam is sealed by hand with a soldering iron set at 400° C. As before, more sacrificial film is applied for compression heat bonding of the assembly. To apply the necessary compressive forces between and around the legs of the bifurcation, scraps of cushion tube material formed into two wedges and covered with polyimide sheeting (0.03 mm thickness, 12.7 mm wide, #TKH-100, available from Fralock Corp., Canoga Park, Calif.) are placed on both sides, between the legs, and under the sacrificial film bonding layer. Retraction forces of the sacrificial film during heat bonding forced the wedges into the space between the legs thereby facilitating bonding the stent frame and graft covering material together. After heat bonding, the sacrificial film and the wedges are removed.

The stent-graft is compacted in the same manner as described in Example 1. The trunk portion is pulled into the die first. The stent-graft plus 0.89 mm guidewire plus capture tube fit within a 10 F delivery tube. The stent graft deploys, it self-expands, to a 31 mm inner diameter in a 36° C. water bath. The device is compacted and restrained within a polyester tube again, this time without a guidewire. The delivery profile is reduced to 9 F. The stent-graft deploys (self-expands) to a 30 mm inner diameter in a 40° C. water bath. Gently pulling it over a tapered mandrel increases its inner diameter to 31 mm.

The a:b ratio of this device ranges from 9.5:1 to 10.6:1.

EXAMPLE 5

Another main body component of a 31 mm (trunk inner diameter) by 12 mm (limb inner diameters) bifurcated stent-graft is constructed using polyester material as the stent covering material. The stent portion is constructed using 0.20 mm, 40–45% cold worked NiTi (nitinol) wire (SE 508; Nitinol Devices & Components, Fremont, Calif.). Yellow polyester film (PES 30/25, available from Saatitech, Inc., Somers, N.Y.) is employed as the stent covering. The polyester material is approximately 0.046 mm thick. The stent member is formed and heat treated in the manner described above in Example 4. The stent covering is attached to the inner surface of the stent frame with CV-8 Sutures (available from W. L. Gore & Associates, Inc., Flagstaff, Ariz.), using a running stitch and tying the ends of the of the sutures together.

As in Example 4, the device is pulled down into a tapered fixture and contained within a capture tube containing a removable polyester inner liner. A long tail of the polyester fabric material is used to pull the stent-graft through the fixture.

The delivery tube inner and outer diameter dimensions are 3.28 mm and 3.33 mm, respectively. The stent-graft main body component plus 0.89 mm wire plus polyester tube (delivery tube) fit within a 10 F hole. The stent-graft deploys to a 31 mm inner diameter in a 40° C. water bath.

The a:b ratio is 9.5:1.

The stent-graft is then compacted again without a guidewire. The stent-graft is pulled into a delivery tube possessing inner and outer diameter dimensions of 2.91 mm and 2.97 mm, respectively. The stent-graft plus delivery tube fit within a 9 F hole and deployed (self-expanded) at 36° C. to 30.5 mm. Gently pulling it over a tapered mandrel increases its diameter to 31 mm.

The a:b ratio is 10.6:1.

EXAMPLE 6

A 23 mm (trunk inner diameter) by 13 mm (limb inner diameters) bifurcated stent-graft main body component is constructed using 0.20 mm diameter, 40–45% cold worked NiTi (nitinol) wire (SE 508; Nitinol Devices & Components, Fremont, Calif.) and ePTFE as the stent covering material. The stent member is formed and heat treated in the manner described above in Example 4. This stent-graft component is made in the same manner, with the same materials, as described in Example 4 following the steps outlined in Table 1.

As in Example 4, the device is pulled down into a tapered fixture and contained within a capture tube containing a removable polyester inner liner. The stent-graft main body component plus 0.89 mm guidewire plus polyester tube (delivery tube) fit within a 6 F hole. The device is deployed, allowed to self-expand, in a 36° C. water bath. The trunk deploys to an inner diameter of 21 mm. Gently pulling the stent-graft over a tapered mandrel increases its inner diameter to 23 mm.

The a:b ratio for this device is 11.7:1.

EXAMPLE 7

A 3.2 mm inner diameter stent-graft is created using ePTFE film and 0.10 mm diameter, 40–45% cold worked NiTi (nitinol) wire (SE 508; Nitinol Devices & Components, Fremont, Calif.). With the exception of the means of attaching the film to the stent frame and the use of 6.35 mm wide as opposed to wider sacrificial film, this stent-graft is made in the same manner, with the same materials, as described in Example 1 following the steps outlined in Table 2. This table also describes properties of the stent-grafts of this and other examples.

The stent frame is powder coated with fluorinated ethylene propylene (FEP) powder (NC1500, available from Daikin Industries, Ltd., Osaka, Japan). FEP powder is placed and stirred in a kitchen blender to create a fine fog of FEP dust. The wire stent frame is cooled with a refrigerant spray, then placed in the fog, thereby coating the FEP to the wire. The FEP is then heat bonded to the wire by placing the coated stent frame into a convection oven set at 320° C. for 3 minutes. The FEP coating enhanced later bonding of the cover film to the stent frame.

The device is pulled down into a tapered fixture and contained within a capture tube containing a removable polyester inner liner as described in Example 1. The stent-graft plus 0.46 mm guidewire plus delivery tube fit within a 3 F hole. A 36° C. water bath is used to deploy the stent-graft. The device is deployed, then compacted again without a guidewire. This time the device plus capture tube fit within a 2.3 F hole. The stent-graft is deployed again in the 36° C. water bath.

The stent-graft exhibits an a:b ratio ranging from 3.4:1 to 4.5:1.

TABLE 2

| | Example 7 | Example 8 | Example 9 |
|---|---|---|---|
| Deployed ID | 3.2 mm | 2 mm | 3 mm |
| Number of Apices | 4 | 3 | 8 |
| Wire Diameter | 0.10 mm | 0.10 mm | [tube thickness = 0.11 mm] |
| Stent Frame Treatment | 6 minutes @ 450° C. | 6 minutes @ 450° C. | 6 minutes @ 450° C. |
| FEP Heat Treatment | 3 minutes @ 320° C. | 3 minutes @ 320° C. | 3 minutes @ 320° C. |
| Cushion Tube/Mandrel | OD = 3.2 mm | OD = 2 mm | OD = 3 mm |
| Inner Release Film | 1 layer | 1 layer | 1 layer |
| Inner Long. Film | 2 layers | 2 layers | 3 layers |
| Inner Circum. Film | n/a | n/a | 1 layer |
| Stent Frame | wire | wire | cut tube |
| Outer Circum. Film | 1 layer | 1 layer | n/a |
| Outer Long. Film | 1 layer | 1 layer | n/a |
| Outer Comp. Film | yes | yes | n/a |
| heat bonding | 5 minutes @ 380° C. | 4 minutes @ 380° C. | 5 minutes @ 380° C. |
| Delivery Tube Dimensions (in mm) [ID/OD] | 3 F: 0.94/1.00 2.3 F: 0.71/0.76 | 2 F: 0.61/0.66 2.5 F: 0.76/0.81 | n/a |
| Guidewire Diameter/Delivery Profile | 0.46 mm/3 F no wire/2.3 F | no wire/2 F 0.30 mm/2.5 F | no wire/4.2 F |
| a:b Ratio | 3.4:1 4.5:1 | 3.3:1 2.6:1 | 2.1:1 |

Key: "n/a" indicates not applicable; "ID" indicates inner diameter; "OD" indicates outer diameter; "Number of apices" indicates the number of exposed apices at an end of a graft; "Long." indicates longitudinal; "Circum." indicates circumferential; "Comp." indicates compression; "Delivery profile" indicates smallest sized hole through which the compacted device plus delivery tube can fit; "a" indicates deployed dimension in mm; "b" indicates compacted dimension in mm.

EXAMPLE 8

A 2 mm inner diameter stent-graft is constructed using 0.10 mm nitinol wire (SE 508; 40–45% cold worked; Nitinol Devices & Components, Fremont, Calif.) and an expanded PTFE film. This stent-graft is made in the same manner, with the same materials, as described in Example 7 following the steps outlined in Table 2. FEP is coated onto the stent frame in the same manner as described in Example 7, as well.

The device is pulled down into a tapered fixture and contained within a capture tube containing a removable polyester inner liner as described in Example 7 and Table 2. The stent-graft without a guidewire plus delivery tube fit within a 2 F hole. The device is deployed in a 36° C. water bath, then compacted again, with a 0.30 mm guidewire. This time the device plus capture tube fits within a 2.5 F hole. It deploys (self-expands) to a 2 mm inner diameter in a 40° C. water bath.

The a:b ratio for this stent-graft ranges from 2.6:1 to 3.3:1.

EXAMPLE 9

Figure 28:
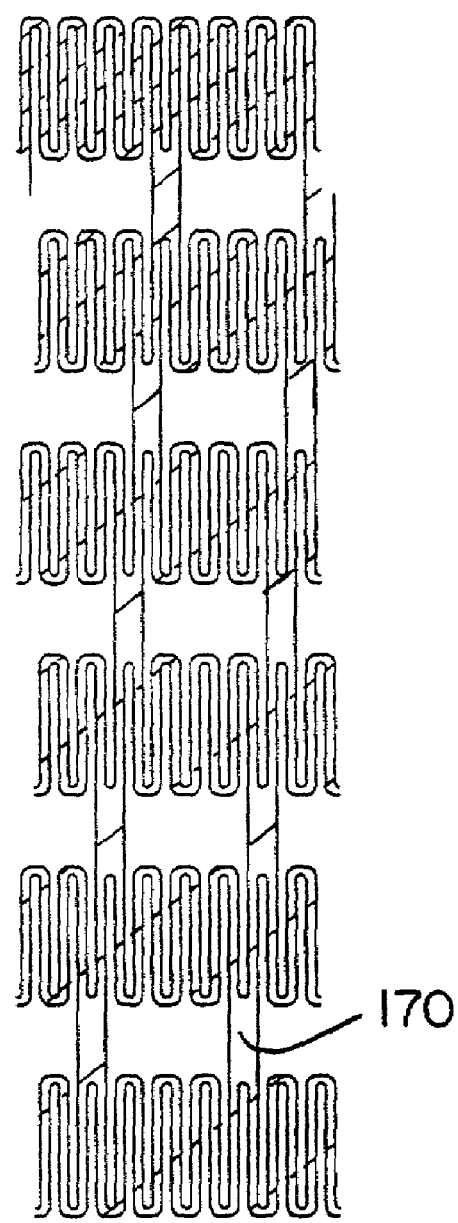
FIG. 28 is a flat pattern configuration of a stent element of the present invention cut from a metal tube.

For this example a section of nitinol tubing (0.11 mm wall thickness, 1.30 mm outer diameter, available from Nitinol Devices & Components, Fremont, Calif.) is machined into a configuration similar to the helical pattern of serpentine bends of wire in the other examples. The stent element 170 is illustrated in FIG. 28. The stent pattern is cut from the nitinol tube using a NdYag laser (available from Laserage, Waukegan, Ill.). The laser removes material from the tubing to leave only a framework skeleton that serves as the stent frame. The laser machined tube is then chilled with a refrigerant spray and stretched up on a tapered mandrel to achieve a 3.0 mm inner diameter.

The stent frame is next subjected to the stent frame (heat) treatment described in Table 2, then quenched in water, in order to set the stent frame at this larger, deployed state, diameter. The stent frame is then FEP powder coated in the same manner as described in Example 7. The graft is then fabricated and attached to the stent frame in the same manner, with the same materials, as described in Example 7 following the steps outlined in Table 2.

This self-expanding stent-graft device is pulled down into a tapered fixture and capture tube as described in Example 7 and Table 2, without a liner inside the capture tube. No guidewire is inserted into the lumen prior to compaction. The stent-graft is pulled by grasping a portion of untrimmed covering material extending beyond the end of the stent frame. The stent-graft without a delivery tube fit within a 1.4 mm hole. The stent-graft is deployed from the capture tube at ambient temperature and expands to a 3.0 mm inner diameter.

The a:b ratio for this stent-graft is 2.1:1.

EXAMPLE 10

Commercially available 26 mm and 40 mm inner diameter thoracic aortic stent-grafts (Thoracic EXCLUDER™ Endovascular Prosthesis, W. L. Gore and Associates, Inc., Flagstaff, Ariz.) are also subjected to some of the inventive compaction techniques to determine if their delivery profiles could be reduced beyond current compacted dimensions. Presently, the manufacturer suggests that Introducer sheaths sized 22 F and 24 F be used with these 26 mm and 40 mm devices, respectively.

The outer sealing cuffs are removed from these devices prior to any testing. A 26 mm device without any wire inserted into its lumen, is pulled through a funnel-shaped tapered die into a capture tube as described in Example 1, except that a two part tapered die is used and and no delivery tube liner is present inside the capture tube.

Figure 29:
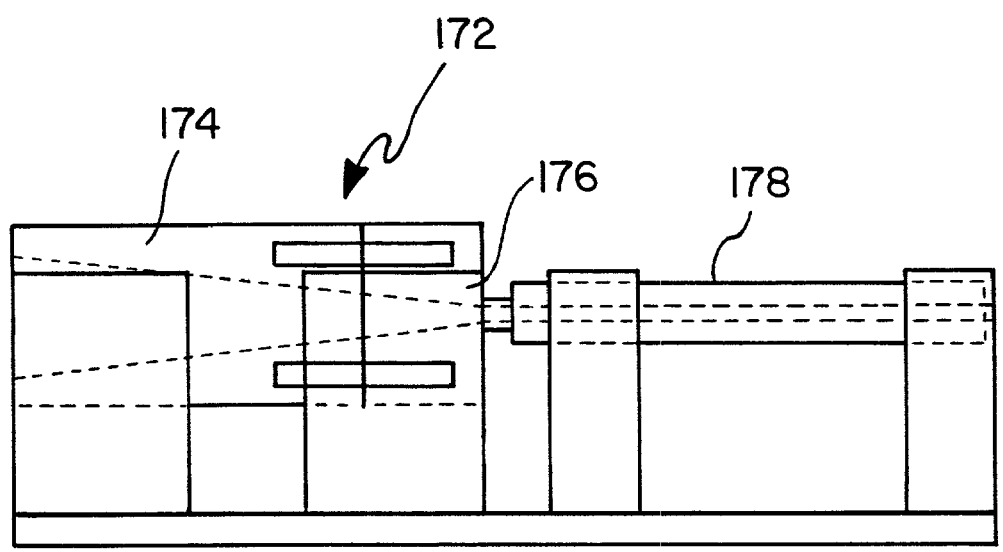
FIG. 29 is a side elevation view of another embodiment of apparatus used to compact stent-grafts of the present invention, this embodiment employing a two-stage tapered die.

As is illustrated in FIG. 29, a two part die 172 is employed having a first stage funnel section 174 and a second stage funnel section 176. The first stage section 174 has an included angle of 12°, the second stage section 176 has an included angle of 12.4°. The device is pulled into successively smaller capture tubes 178. Containment within a 3.43 mm capture tube indicates that it will fit within an 11 F hole. A 36° C. water bath is used to deploy the stent-graft.

The graft is deployed to 24 mm, increasing to 26 mm when gently pulled over a tapered mandrel.

Another 26 mm device, also without a guidewire, is pulled through a fluted tapered die, thereby fitting into a 3.18 mm capture tube, hence it fit within a 10 F hole. The second stage section 176 is modified to create flutes in the manner previously described with reference to FIGS. 16a through 16c. Eight (8) flutes are created, matching the number of apices of the device.

Using the fluted compaction techniques previously described, the delivery profile of the 26 mm devices is reduced by 1 F. A 36° C. water bath is used to deploy the stent-graft. The graft is deployed to 24 mm, increasing to 26 mm when gently pulled over a tapered mandrel.

The use of the fluted die increases the a:b ratio from 7.6:1 to 8.2:1.

The 40 mm device without a guidewire is subjected to the same compaction process using a two part smooth tapered die as described in FIG. 29. The first stage section 174 and second stage section 176 have included angles of 12° and 7.2°, respectively. The device is successively pulled into capture tubes 178 possessing inner diameters of 6.35 mm 6.00 mm, and 5.33 mm. The size of the device precluded it from being drawn into a 5.00 mm inner diameter capture tube. This 40 mm device is subsequently pulled through the 5.33 mm capture tube a total of five times to prepare it for pulling into a smaller capture tube. The force required to pull the device through this capture tube decreases from 27 kg for the first pull to 18 kg for the last pull. The decrease in force suggests that the device could be pulled into a smaller capture tube without damaging the device. The device is then successfully pulled into a 5.00 mm capture tube. This step of repeatedly pulling the stent-graft through a same sized capture tube enables it to be compacted further.

The a:b ratio for this stent-graft is 8:1.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A method of compacting an endoprosthesis into a compacted dimension comprising
    providing a self-expanding endoprosthesis comprising a stent-element;
    providing at least one internally tapered die proportioned to compact the endoprosthesis, the tapered die including multiple raised flutes and grooves therein to define a tapered surface;
    passing the endoprosthesis through the tapered die to reduce its dimensions, the raised flutes and grooves causing the endoprosthesis to fold into uniform pleats in its compacted dimension.

2. The method of claim 1 that further comprises
    passing the endoprosthesis through the tapered die at least one additional time.

3. The method of claim 2 that further comprises allowing the endoprosthesis to expand before passing it through the at least one tapered die at least one additional time.

4. The method of claim 1 that further comprises
    subsequently passing the endoprosthesis through a second taper die having a smaller diameter.

5. The method of claim 1 that further comprises passing the endoprosthesis through a tapered die having a larger diameter prior to compacting in the at least one tapered die.

6. The method of claim 1 that further comprises
    providing the stent-element with forward facing apices and rearward facing apices;
    providing a tether line attached to or aligned with one or more of the apices;

pulling the endoprosthesis through the at least one tapered die using the tether line.

7. The method of claim 6 that further comprises
providing an actuation mechanism;
attaching the tether line to the actuation mechanism to pull the endoprosthesis through the at least one tapered die.

8. The method of claim 6 that further comprises
providing multiple tether lines;
aligning the tether lines with only forward facing apices so that when the tether lines are pulled through the grooves only the forward facing apices are visible on the outside of the compressed endoprosthesis.

9. The method of claim 1 that further comprises
positioning the flutes evenly around the tapered die so as to produce a uniform spacing of pleats around the compressed endoprosthesis.

10. The method of claim 9 that further comprises
providing a uniform spacing of grooves within the at least one endoprosthesis;
providing a tether line to correspond with each groove; and
passing the endoprosthesis through the tapered die using the tether lines.

11. The method of claim 1 that further comprises cooling the endoprosthesis prior to passing through the tapered die.

* * * * *